US011857767B2

(12) United States Patent
Bar-El et al.

(10) Patent No.: US 11,857,767 B2
(45) Date of Patent: Jan. 2, 2024

(54) INJECTOR USABLE WITH DIFFERENT DIMENSION CARTRIDGES

(71) Applicant: West Pharma. Services IL, Ltd., Ra'anana (IL)

(72) Inventors: Yossi Bar-El, Beit Arye (IL); Igor Isakov, Rehovot (IL); Lior Barchen, Gani Tal (IL)

(73) Assignee: West Pharma. Services IL, LTD., Ra'anana (IL)

( * ) Notice: Subject to any disclaimer, the term of this patent is extended or adjusted under 35 U.S.C. 154(b) by 472 days.

(21) Appl. No.: 16/955,321

(22) PCT Filed: Dec. 20, 2018

(86) PCT No.: PCT/US2018/066660
§ 371 (c)(1),
(2) Date: Jun. 18, 2020

(87) PCT Pub. No.: WO2019/126421
PCT Pub. Date: Jun. 27, 2019

(65) Prior Publication Data
US 2021/0001047 A1    Jan. 7, 2021

Related U.S. Application Data

(60) Provisional application No. 62/609,740, filed on Dec. 22, 2017.

(51) Int. Cl.
*A61M 5/24* (2006.01)
*A61M 5/34* (2006.01)

(52) U.S. Cl.
CPC .......... *A61M 5/2466* (2013.01); *A61M 5/345* (2013.01); *A61M 2005/244* (2013.01);
(Continued)

(58) Field of Classification Search
CPC ................ A61M 5/2466; A61M 5/345; A61M 2005/2407; A61M 2005/2433;
(Continued)

(56) References Cited

U.S. PATENT DOCUMENTS 1,795,630 A    3/1931 Wilson
2,860,635 A    11/1958 Wilburn
(Continued)

FOREIGN PATENT DOCUMENTS

CN    1224341 A    7/1999
CN    1376524        10/2002
(Continued)

OTHER PUBLICATIONS

Int'l Search Report and Written Opinion dated Apr. 23, 2019 in Int'l Application No. PCT/US2018/066660.
(Continued)

*Primary Examiner* — Amber R Stiles
*Assistant Examiner* — Hong-Van N Trinh
(74) *Attorney, Agent, or Firm* — Blank Rome LLP

(57) ABSTRACT

An injector includes a body, an injection needle movably mounted to the body and a pathway within the body sized for receiving either of a first cartridge or a differently dimensioned second cartridge therein. The pathway includes a coupler mounted at a distal end that is engageable with the first cartridge or the second cartridge for to fluidly connect with the injection needle. At least two adapter collars are mounted within the pathway. A first adapter collar is configured to receive either one of the two cartridges therethrough upon insertion into the pathway, and configured to engage a portion of the first cartridge to stabilize the first cartridge within the pathway. A second adapter collar is also configured to receive either one of the two cartridges therethrough upon insertion into the pathway, but configured to
(Continued)

engage a portion of the second cartridge to stabilize the second cartridge within the pathway.

19 Claims, 9 Drawing Sheets

(52) U.S. Cl.
CPC ............... *A61M 2005/247* (2013.01); *A61M 2005/2407* (2013.01)

(58) Field of Classification Search
CPC .... A61M 2005/244; A61M 2005/2444; A61M 2005/2437; A61M 2005/247; A61M 2005/2414; A61M 2005/2474; A61M 5/2459; A61M 2005/14252
See application file for complete search history.

(56) References Cited

U.S. PATENT DOCUMENTS

| | | |
|---|---|---|
| 3,203,269 A | 8/1965 | Perrine |
| 3,212,685 A | 10/1965 | Swan |
| 3,782,365 A | 1/1974 | Pinna |
| 3,794,028 A | 2/1974 | Mueller |
| 3,946,732 A | 3/1976 | Hurscham |
| 3,994,295 A | 11/1976 | Wulff |
| 4,026,128 A | 5/1977 | Blanco |
| 4,167,663 A | 9/1979 | Granzow, Jr. |
| 4,195,636 A | 4/1980 | Behnke |
| 4,218,724 A | 8/1980 | Kaufman |
| 4,273,122 A | 6/1981 | Whitney |
| 4,300,554 A | 11/1981 | Hessberg |
| 4,396,385 A | 8/1983 | Kelly |
| 4,403,987 A | 9/1983 | Gottinger |
| 4,435,173 A | 3/1984 | Siposs |
| 4,465,478 A | 8/1984 | Sabelman |
| 4,565,543 A | 1/1986 | Bekkering |
| 4,585,439 A | 4/1986 | Michel |
| 4,599,082 A | 7/1986 | Grimard |
| 4,601,702 A | 7/1986 | Hudson |
| 4,634,426 A | 1/1987 | Kamen |
| 4,685,903 A | 8/1987 | Cable |
| 4,689,043 A | 8/1987 | Bisha |
| 4,698,055 A | 10/1987 | Sealfon |
| 4,810,215 A | 3/1989 | Kaneko |
| 4,850,966 A | 7/1989 | Grau |
| 4,867,743 A | 9/1989 | Vaillancourt |
| 4,886,499 A | 12/1989 | Cirelli |
| 4,908,014 A | 3/1990 | Kroyer |
| 4,919,596 A | 4/1990 | Slate |
| 4,929,241 A | 5/1990 | Kulli |
| 4,950,235 A | 8/1990 | Slate |
| 4,950,246 A | 8/1990 | Muller |
| 4,955,865 A | 9/1990 | Steiner |
| D322,671 S | 12/1991 | Szwarc |
| 5,090,877 A | 2/1992 | D Silva |
| 5,109,850 A | 5/1992 | Blanco |
| 5,112,317 A | 5/1992 | Michel |
| 5,131,816 A | 7/1992 | Brown |
| 5,183,469 A | 2/1993 | Capaccio |
| 5,190,521 A | 3/1993 | Hubbard |
| 5,254,096 A | 10/1993 | Rondelet |
| 5,300,045 A | 4/1994 | Plassche, Jr. |
| 5,342,313 A | 8/1994 | Campbell |
| 5,348,544 A | 9/1994 | Sweeney |
| 5,354,287 A | 10/1994 | Wacks |
| 5,364,364 A | 11/1994 | Kasvikis |
| 5,366,498 A | 11/1994 | Brannan |
| 5,383,865 A | 1/1995 | Michel |
| 5,411,482 A | 5/1995 | Campbell |
| 5,445,621 A | 8/1995 | Poli |
| 5,478,315 A | 12/1995 | Brothers |
| 5,482,446 A | 1/1996 | Williamson |
| 5,496,274 A | 3/1996 | Graves |
| 5,501,665 A | 3/1996 | Jhuboo |
| 5,505,709 A | 4/1996 | Funderburk |
| D372,098 S | 7/1996 | Lattin |
| 5,558,639 A | 9/1996 | Gangemi |
| 5,562,686 A | 10/1996 | Sauer |
| 5,593,390 A | 1/1997 | Castellano |
| 5,616,132 A | 4/1997 | Newman |
| 5,643,218 A | 7/1997 | Lynn |
| 5,645,955 A | 7/1997 | Maglica |
| 5,647,853 A | 7/1997 | Feldmann |
| 5,658,133 A | 8/1997 | Anderson |
| 5,662,678 A | 9/1997 | Macklin |
| 5,672,160 A | 9/1997 | Oesterlind |
| D384,745 S | 10/1997 | Lattin |
| 5,690,618 A | 11/1997 | Smith |
| D393,314 S | 4/1998 | Meisner |
| 5,741,227 A | 4/1998 | Sealfon |
| 5,766,186 A | 6/1998 | Faraz |
| 5,779,676 A | 7/1998 | Kriesel |
| 5,795,675 A | 8/1998 | Maglica |
| 5,800,420 A | 9/1998 | Gross |
| 5,807,375 A | 9/1998 | Gross |
| 5,814,020 A | 9/1998 | Gross |
| 5,820,406 A | 10/1998 | Hetherington |
| 5,830,187 A | 11/1998 | Kriesel |
| 5,836,920 A | 11/1998 | Robertson |
| 5,848,991 A | 12/1998 | Gross |
| 5,851,197 A | 12/1998 | Marano |
| 5,858,001 A | 1/1999 | Tsals |
| 5,858,008 A | 1/1999 | Capaccio |
| 5,865,804 A | 2/1999 | Bachynsky |
| 5,868,710 A | 2/1999 | Battiato |
| 5,925,018 A | 7/1999 | Ungerstedt |
| 5,931,814 A | 8/1999 | Alex |
| 5,941,850 A | 8/1999 | Shah |
| 5,948,392 A | 9/1999 | Haslwanter |
| 5,954,697 A | 9/1999 | Srisathapat |
| 5,957,895 A | 9/1999 | Sage |
| 5,968,011 A | 10/1999 | Gullak |
| 5,993,423 A | 11/1999 | Choi |
| 5,997,501 A | 12/1999 | Gross |
| 6,004,297 A | 12/1999 | Steenfeldt-Jensen |
| 6,033,245 A | 3/2000 | Yamkovoy |
| 6,033,377 A | 3/2000 | Rasmussen |
| 6,064,797 A | 5/2000 | Crittendon |
| 6,074,369 A | 6/2000 | Sage |
| 6,117,575 A | 9/2000 | Dinsdale |
| 6,149,614 A | 11/2000 | Dunshee |
| 6,160,487 A | 12/2000 | DeLuca |
| 6,175,688 B1 | 1/2001 | Cassidy |
| 6,186,982 B1 | 2/2001 | Gross |
| 6,200,289 B1 | 3/2001 | Hochman |
| 6,200,296 B1 | 3/2001 | Dibiasi |
| 6,224,569 B1 | 5/2001 | Brimhall |
| 6,248,093 B1 | 6/2001 | Moberg |
| 6,277,095 B1 | 8/2001 | Kriesel |
| 6,277,098 B1 | 8/2001 | Klitmose |
| 6,277,099 B1 | 8/2001 | Strowe |
| 6,287,283 B1 | 9/2001 | Henrik |
| 6,293,925 B1 | 9/2001 | Safabash |
| 6,302,633 B1 | 10/2001 | Poe |
| 6,305,908 B1 | 10/2001 | Hermann |
| 6,336,729 B1 | 1/2002 | Pavelle |
| 6,345,968 B1 | 2/2002 | Shupe |
| 6,362,591 B1 | 3/2002 | Moberg |
| 6,377,848 B1 | 4/2002 | Garde |
| 6,391,005 B1 | 5/2002 | Lum |
| 6,423,029 B1 | 7/2002 | Elsberry |
| 6,423,036 B1 | 7/2002 | Van Huizen |
| D465,026 S | 10/2002 | May |
| 6,458,102 B1 | 10/2002 | Mann |
| 6,485,461 B1 | 11/2002 | Mason |
| 6,485,465 B2 | 11/2002 | Moberg |
| 6,500,150 B1 | 12/2002 | Gross |
| 6,503,231 B1 | 1/2003 | Prausnitz |
| 6,511,336 B1 | 1/2003 | Turek |
| 6,517,517 B1 | 2/2003 | Farrugia |
| D471,274 S | 3/2003 | Diaz |
| D471,983 S | 3/2003 | Hippolyte |

(56) References Cited

U.S. PATENT DOCUMENTS

| | | |
|---|---|---|
| 6,530,901 B1 | 3/2003 | Tsukada |
| 6,555,986 B2 | 4/2003 | Moberg |
| 6,558,351 B1 | 5/2003 | Steil |
| 6,558,365 B2 | 5/2003 | Zinger |
| 6,589,229 B1 | 7/2003 | Connelly |
| 6,595,956 B1 | 7/2003 | Gross |
| 6,595,960 B2 | 7/2003 | West |
| 6,599,272 B1 | 7/2003 | Hjertman |
| 6,632,201 B1 | 10/2003 | Mathias |
| 6,645,181 B1 | 11/2003 | Lavi |
| 6,652,482 B2 | 11/2003 | Hochman |
| 6,656,158 B2 | 12/2003 | Mahoney |
| 6,656,159 B2 | 12/2003 | Flaherty |
| 6,659,980 B2 | 12/2003 | Moberg |
| 6,673,033 B1 | 1/2004 | Sciulli |
| 6,679,862 B2 | 1/2004 | Diaz |
| 6,689,118 B2 | 2/2004 | Alchas |
| 6,699,218 B2 | 3/2004 | Flaherty |
| 6,722,916 B2 | 4/2004 | Buccinna |
| 6,736,796 B2 | 5/2004 | Shekalim |
| 6,740,059 B2 | 5/2004 | Flaherty |
| 6,743,211 B1 | 6/2004 | Prausnitz |
| 6,749,587 B2 | 6/2004 | Flaherty |
| 6,752,787 B1 | 6/2004 | Causey, III |
| 6,768,425 B2 | 7/2004 | Flaherty |
| 6,786,890 B2 | 9/2004 | Preuthun |
| 6,800,071 B1 | 10/2004 | McConnell |
| 6,805,687 B2 | 10/2004 | Dextradeur |
| 6,810,350 B2 | 10/2004 | Blakley |
| 6,824,529 B2 | 11/2004 | Gross |
| 6,843,782 B2 | 1/2005 | Gross |
| 6,854,620 B2 | 2/2005 | Ramey |
| 6,905,298 B1 | 6/2005 | Haring |
| 6,908,452 B2 | 6/2005 | Diaz |
| 6,950,028 B2 | 9/2005 | Zweig |
| 6,960,192 B1 | 11/2005 | Flaherty |
| 6,972,002 B2 | 12/2005 | Thorne |
| 6,997,727 B1 | 2/2006 | Legrady |
| 7,001,360 B2 | 2/2006 | Veasey |
| 7,034,223 B2 | 4/2006 | Fan |
| 7,048,715 B2 | 5/2006 | Diaz |
| 7,060,054 B2 | 6/2006 | Nissels |
| 7,060,059 B2 | 6/2006 | Keith |
| 7,097,637 B2 | 8/2006 | Triplett |
| 7,128,727 B2 | 10/2006 | Flaherty |
| 7,144,384 B2 | 12/2006 | Gorman |
| 7,193,521 B2 | 3/2007 | Moberg |
| 7,214,209 B2 | 5/2007 | Mazzoni |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer |
| 7,267,669 B2 | 9/2007 | Staunton |
| 7,291,132 B2 | 11/2007 | DeRuntz |
| 7,291,159 B2 | 11/2007 | Schmelzeisen-Redeker |
| 7,303,549 B2 | 12/2007 | Flaherty |
| 7,344,385 B2 | 3/2008 | Chen |
| 7,364,570 B2 | 4/2008 | Gerondale |
| 7,377,907 B2 | 5/2008 | Shekalim |
| 7,390,314 B2 | 6/2008 | Stutz, Jr. |
| 7,407,493 B2 | 8/2008 | Cane |
| D578,210 S | 10/2008 | Muta |
| 7,455,663 B2 | 11/2008 | Bikovsky |
| 7,465,290 B2 | 12/2008 | Reilly |
| 7,488,181 B2 | 2/2009 | Van Haaster |
| 7,497,842 B2 | 3/2009 | Diaz |
| 7,501,587 B2 | 3/2009 | English |
| 7,503,786 B2 | 3/2009 | Kato |
| 7,524,304 B2 | 4/2009 | Genosar |
| 7,530,964 B2 | 5/2009 | Lavi |
| 7,547,281 B2 | 6/2009 | Hayes |
| 7,563,253 B2 | 7/2009 | Tanner |
| 7,565,208 B2 | 7/2009 | Harris |
| 7,569,050 B2 | 8/2009 | Moberg |
| D600,341 S | 9/2009 | Loerwald |
| 7,585,287 B2 | 9/2009 | Bresina |
| 7,588,559 B2 | 9/2009 | Aravena |
| 7,589,974 B2 | 9/2009 | Grady |
| D602,155 S | 10/2009 | Foley |
| D602,586 S | 10/2009 | Foley |
| D604,835 S | 11/2009 | Conley |
| 7,621,893 B2 | 11/2009 | Moberg |
| 7,628,770 B2 | 12/2009 | Ethelfeld |
| 7,628,772 B2 | 12/2009 | McConnell |
| 7,628,782 B2 | 12/2009 | Adair |
| 7,637,891 B2 | 12/2009 | Wall |
| 7,637,899 B2 | 12/2009 | Woolston |
| 7,641,649 B2 | 1/2010 | Moberg |
| 7,660,627 B2 | 2/2010 | McNichols |
| 7,678,079 B2 | 3/2010 | Shermer |
| 7,682,338 B2 | 3/2010 | Griffin |
| 7,686,787 B2 | 3/2010 | Moberg |
| 7,699,829 B2 | 4/2010 | Harris |
| 7,699,833 B2 | 4/2010 | Moberg |
| 7,704,088 B2 | 4/2010 | Sakamoto |
| 7,704,227 B2 | 4/2010 | Moberg |
| 7,704,229 B2 | 4/2010 | Moberg |
| 7,704,231 B2 | 4/2010 | Pongpairochana |
| 7,708,717 B2 | 5/2010 | Estes |
| 7,713,238 B2 | 5/2010 | Mernoe |
| 7,713,240 B2 | 5/2010 | Istoc |
| 7,717,913 B2 | 5/2010 | Novak |
| 7,722,574 B2 | 5/2010 | Toman |
| 7,736,344 B2 | 6/2010 | Moberg |
| 7,744,589 B2 | 6/2010 | Mounce |
| 7,749,194 B2 | 7/2010 | Edwards |
| 7,753,879 B2 | 7/2010 | Mernoe |
| 7,766,873 B2 | 8/2010 | Moberg |
| 7,776,030 B2 | 8/2010 | Estes |
| 7,780,636 B2 | 8/2010 | Radmer |
| 7,780,637 B2 | 8/2010 | Jerde |
| 7,789,857 B2 | 9/2010 | Moberg |
| 7,789,862 B2 | 9/2010 | Thorne, Jr. |
| 7,794,426 B2 | 9/2010 | Briones |
| 7,801,599 B2 | 9/2010 | Young |
| 7,806,868 B2 | 10/2010 | De Polo |
| 7,815,622 B2 | 10/2010 | Istoc |
| 7,828,528 B2 | 11/2010 | Estes |
| 7,837,659 B2 | 11/2010 | Bush, Jr. |
| 7,846,132 B2 | 12/2010 | Gravesen |
| 7,850,661 B2 | 12/2010 | Chevallier |
| 7,854,723 B2 | 12/2010 | Hwang |
| 7,857,131 B2 | 12/2010 | Vedrine |
| 7,879,025 B2 | 2/2011 | Jacobson |
| 7,879,026 B2 | 2/2011 | Estes |
| 7,892,206 B2 | 2/2011 | Moberg |
| 7,918,825 B2 | 4/2011 | O'Connor |
| 7,918,843 B2 | 4/2011 | Genosar |
| 7,935,104 B2 | 5/2011 | Yodfat |
| 7,935,105 B2 | 5/2011 | Miller |
| 7,938,803 B2 | 5/2011 | Mernoe |
| 7,955,305 B2 | 6/2011 | Moberg |
| 7,967,784 B2 | 6/2011 | Pongpairochana |
| 7,967,795 B1 | 6/2011 | Cabiri |
| 7,981,105 B2 | 7/2011 | Adair |
| 7,988,683 B2 | 8/2011 | Adair |
| 7,993,300 B2 | 8/2011 | Nyholm |
| 7,993,301 B2 | 8/2011 | Boyd |
| 7,998,111 B2 | 8/2011 | Moberg |
| 8,021,357 B2 | 9/2011 | Tanaka |
| 8,025,658 B2 | 9/2011 | Chong |
| 8,029,469 B2 | 10/2011 | Ethelfeld |
| 8,034,019 B2 | 10/2011 | Nair |
| 8,038,666 B2 | 10/2011 | Triplett |
| 8,057,431 B2 | 11/2011 | Woehr |
| 8,057,436 B2 | 11/2011 | Causey |
| 8,062,253 B2 | 11/2011 | Nielsen |
| 8,062,257 B2 | 11/2011 | Moberg |
| 8,065,096 B2 | 11/2011 | Moberg |
| 8,066,694 B2 | 11/2011 | Wagener |
| D650,079 S | 12/2011 | Presta |
| D650,903 S | 12/2011 | Kosinski |
| 8,086,306 B2 | 12/2011 | Katzman |
| D652,503 S | 1/2012 | Cameron, III |

(56) References Cited

U.S. PATENT DOCUMENTS

| | | |
|---|---|---|
| 8,105,279 B2 | 1/2012 | Mernoe |
| 8,114,046 B2 | 2/2012 | Covino |
| 8,114,064 B2 | 2/2012 | Alferness |
| 8,114,066 B2 | 2/2012 | Naef |
| D657,462 S | 4/2012 | Siroky |
| 8,147,446 B2 | 4/2012 | Yodfat |
| 8,152,764 B2 | 4/2012 | Istoc |
| 8,152,770 B2 | 4/2012 | Reid |
| 8,152,779 B2 | 4/2012 | Cabiri |
| 8,152,793 B2 | 4/2012 | Keinaenen |
| 8,157,693 B2 | 4/2012 | Waksmundzki |
| 8,157,769 B2 | 4/2012 | Cabiri |
| 8,162,674 B2 | 4/2012 | Cho |
| 8,162,923 B2 | 4/2012 | Adams |
| 8,167,841 B2 | 5/2012 | Teisen-Simony |
| 8,172,591 B2 | 5/2012 | Wertz |
| 8,172,804 B2 | 5/2012 | Bikovsky |
| 8,182,447 B2 | 5/2012 | Moberg |
| 8,182,462 B2 | 5/2012 | Istoc |
| 8,197,444 B1 | 6/2012 | Bazargan |
| 8,206,351 B2 | 6/2012 | Sugimoto |
| 8,221,356 B2 | 7/2012 | Enggaard |
| 8,226,610 B2 | 7/2012 | Edwards |
| 8,267,893 B2 | 9/2012 | Moberg |
| 8,267,921 B2 | 9/2012 | Yodfat |
| 8,287,520 B2 | 10/2012 | Drew |
| 8,292,647 B1 | 10/2012 | McGrath |
| 8,308,679 B2 | 11/2012 | Hanson |
| 8,323,250 B2 | 12/2012 | Chong |
| 8,348,898 B2 | 1/2013 | Cabiri |
| 8,372,039 B2 | 2/2013 | Mernoe |
| 8,373,421 B2 | 2/2013 | Stefan |
| 8,409,142 B2 | 4/2013 | Causey |
| 8,414,557 B2 | 4/2013 | Istoc |
| 8,414,563 B2 | 4/2013 | Kamen |
| 8,430,847 B2 | 4/2013 | Mernoe |
| D685,083 S | 6/2013 | Schneider |
| 8,465,455 B2 | 6/2013 | Cabiri |
| 8,469,942 B2 | 6/2013 | Kow |
| D687,141 S | 7/2013 | Schneider |
| 8,474,332 B2 | 7/2013 | Bente, IV |
| 8,475,408 B2 | 7/2013 | Mernoe |
| 8,479,595 B2 | 7/2013 | Vazquez |
| 8,483,980 B2 | 7/2013 | Moberg |
| 8,495,918 B2 | 7/2013 | Bazargan |
| 8,496,862 B2 | 7/2013 | Zelkovich |
| D687,536 S | 8/2013 | Guarraia |
| 8,512,287 B2 | 8/2013 | Cindrich |
| 8,517,987 B2 | 8/2013 | Istoc |
| 8,523,803 B1 | 9/2013 | Favreau |
| D692,552 S | 10/2013 | Lovell |
| 8,556,856 B2 | 10/2013 | Bazargan |
| 8,562,364 B2 | 10/2013 | Lin |
| 8,574,216 B2 | 11/2013 | Istoc |
| 8,603,026 B2 | 12/2013 | Favreau |
| 8,603,027 B2 | 12/2013 | Favreau |
| 8,617,110 B2 | 12/2013 | Moberg |
| 8,628,510 B2 | 1/2014 | Bazargan |
| 8,647,074 B2 | 2/2014 | Moberg |
| 8,647,296 B2 | 2/2014 | Moberg |
| 8,668,672 B2 | 3/2014 | Moberg |
| 8,674,288 B2 | 3/2014 | Hanson |
| 8,679,060 B2 | 3/2014 | Mernoe |
| 8,679,062 B2 | 3/2014 | Yodfat |
| 8,681,010 B2 | 3/2014 | Moberg |
| 8,690,855 B2 | 4/2014 | Alderete, Jr. |
| 8,708,961 B2 | 4/2014 | Field |
| 8,751,237 B2 | 6/2014 | Kubota |
| 8,753,326 B2 | 6/2014 | Chong |
| 8,753,331 B2 | 6/2014 | Murphy |
| 8,764,707 B2 | 7/2014 | Moberg |
| 8,764,723 B2 | 7/2014 | Chong |
| 8,771,222 B2 | 7/2014 | Kanderian, Jr. |
| 8,777,896 B2 | 7/2014 | Starkweather |
| 8,777,924 B2 | 7/2014 | Kanderian, Jr. |
| 8,777,925 B2 | 7/2014 | Patton |
| 8,784,369 B2 | 7/2014 | Starkweather |
| 8,784,370 B2 | 7/2014 | Lebel |
| 8,790,295 B1 | 7/2014 | Sigg |
| 8,795,224 B2 | 8/2014 | Starkweather |
| 8,795,231 B2 | 8/2014 | Chong |
| 8,795,260 B2 | 8/2014 | Drew |
| 8,801,668 B2 | 8/2014 | Ali |
| 8,801,679 B2 | 8/2014 | Iio |
| 8,810,394 B2 | 8/2014 | Kalpin |
| 8,814,379 B2 | 8/2014 | Griffiths |
| 8,827,964 B2 | 9/2014 | Boyd |
| 8,915,882 B2 | 12/2014 | Cabiri |
| 8,920,374 B2 | 12/2014 | Bokelman |
| D723,157 S | 2/2015 | Clemente |
| 8,945,051 B2 | 2/2015 | Schriver |
| 9,061,104 B2 | 6/2015 | Daniel |
| 9,061,110 B2 | 6/2015 | Avery |
| 9,072,827 B2 | 7/2015 | Cabiri |
| 9,079,949 B1 | 7/2015 | Andrien, Jr. |
| 9,089,475 B2 | 7/2015 | Fangrow |
| 9,089,641 B2 | 7/2015 | Kavazov |
| 9,149,575 B2 | 10/2015 | Cabiri |
| 9,181,008 B2 | 11/2015 | Milan |
| D747,799 S | 1/2016 | Norton |
| 9,233,213 B2 | 1/2016 | Olson |
| 9,242,044 B2 | 1/2016 | Markussen |
| 9,278,177 B2 | 3/2016 | Edwards |
| 9,302,089 B2 | 4/2016 | Besko |
| 9,339,610 B2 | 5/2016 | Julian |
| 9,393,365 B2 | 7/2016 | Cabiri |
| 9,421,321 B2 | 8/2016 | Hanson |
| 9,452,255 B2 | 9/2016 | Tieck |
| D768,288 S | 10/2016 | O'Connor |
| 9,463,280 B2 | 10/2016 | Cabiri |
| 9,470,587 B1 | 10/2016 | Greene |
| 9,492,610 B2 | 11/2016 | Cabiri |
| 9,492,618 B2 | 11/2016 | Day |
| D774,640 S | 12/2016 | Tyce |
| 9,511,190 B2 | 12/2016 | Cabiri |
| 9,522,234 B2 | 12/2016 | Cabiri |
| 9,526,826 B2 | 12/2016 | Nagar |
| D776,262 S | 1/2017 | Tyce |
| D776,263 S | 1/2017 | Tyce |
| D776,264 S | 1/2017 | Tyce |
| D776,265 S | 1/2017 | Tyce |
| 9,572,926 B2 | 2/2017 | Cabiri |
| 9,610,404 B2 | 4/2017 | Rotstein |
| 9,682,199 B2 | 6/2017 | Walsh |
| 9,707,335 B2 | 7/2017 | Agard |
| D794,776 S | 8/2017 | Tyce |
| 9,737,655 B2 | 8/2017 | Clemente |
| 9,782,545 B2 | 10/2017 | Gross |
| 9,802,030 B2 | 10/2017 | Clemente |
| D804,019 S | 11/2017 | Costello |
| 9,814,832 B2 | 11/2017 | Agard |
| 9,821,118 B2 | 11/2017 | Adlon |
| D804,650 S | 12/2017 | Costello |
| D805,186 S | 12/2017 | Costello |
| D805,187 S | 12/2017 | Costello |
| D805,188 S | 12/2017 | Costello |
| D805,189 S | 12/2017 | Costello |
| D805,190 S | 12/2017 | Costello |
| 9,844,629 B2 | 12/2017 | Cronenberg |
| 9,861,759 B2 | 1/2018 | Gross |
| D810,278 S | 2/2018 | Cabiri |
| D810,279 S | 2/2018 | Cabiri |
| D811,583 S | 2/2018 | Cabiri |
| D811,584 S | 2/2018 | Cabiri |
| 9,907,911 B2 | 3/2018 | Constantineau |
| 9,931,461 B2 | 4/2018 | Kamen |
| D817,481 S | 5/2018 | Cabiri |
| 9,987,416 B2 | 6/2018 | McNall, III |
| 10,071,196 B2 | 9/2018 | Cabiri |
| 10,137,243 B2 | 11/2018 | Wang |
| 10,149,943 B2 | 12/2018 | Bar-El |
| 10,155,085 B2 | 12/2018 | Gescheit |
| 10,201,692 B2 | 2/2019 | Chang |
| D851,752 S | 6/2019 | Nazzaro |

(56) References Cited

U.S. PATENT DOCUMENTS

| | | |
|---|---|---|
| 10,335,553 B2 | 7/2019 | Bendek |
| 10,391,261 B1 | 8/2019 | Glammeier |
| D865,945 S | 11/2019 | Nazzaro |
| 10,463,847 B2 | 11/2019 | Shaked |
| 10,639,417 B2 | 5/2020 | Roberts |
| 10,688,243 B2 | 6/2020 | Cabiri |
| 10,765,808 B2 | 9/2020 | Day |
| 10,780,232 B2 | 9/2020 | Jugl |
| 10,792,435 B2 | 10/2020 | Davis |
| 10,835,690 B2 | 11/2020 | Xiang |
| 11,103,651 B2 | 8/2021 | Sanders |
| 11,110,230 B2 | 9/2021 | Maxfield |
| 11,179,518 B2 | 11/2021 | Gertsenchtein |
| 11,207,465 B2 | 12/2021 | Bar-El |
| 2001/0025168 A1 | 9/2001 | Gross |
| 2001/0041869 A1 | 11/2001 | Causey |
| 2002/0010423 A1 | 1/2002 | Gross |
| 2002/0029018 A1 | 3/2002 | Jeffrey |
| 2002/0040208 A1 | 4/2002 | Flaherty |
| 2002/0043951 A1 | 4/2002 | Moberg |
| 2002/0055711 A1 | 5/2002 | Lavi |
| 2002/0065488 A1 | 5/2002 | Suzuki |
| 2002/0072733 A1 | 6/2002 | Flaherty |
| 2002/0107487 A1 | 8/2002 | Preuthun |
| 2002/0123740 A1 | 9/2002 | Flaherty |
| 2002/0161332 A1 | 10/2002 | Ramey |
| 2002/0169215 A1 | 11/2002 | Meng |
| 2002/0188419 A1 | 12/2002 | Slate |
| 2003/0009133 A1 | 1/2003 | Ramey |
| 2003/0109827 A1 | 6/2003 | Gilad |
| 2003/0125671 A1 | 7/2003 | Aramata |
| 2003/0135159 A1 | 7/2003 | Daily |
| 2003/0160683 A1 | 8/2003 | Blomquist |
| 2003/0171717 A1 | 9/2003 | Farrugia |
| 2003/0181868 A1 | 9/2003 | Swenson |
| 2003/0199825 A1 | 10/2003 | Flaherty |
| 2003/0199827 A1 | 10/2003 | Thorne |
| 2003/0236498 A1 | 12/2003 | Gross |
| 2004/0002682 A1 | 1/2004 | Kovelman |
| 2004/0010207 A1 | 1/2004 | Flaherty |
| 2004/0015131 A1 | 1/2004 | Flaherty |
| 2004/0064088 A1 | 4/2004 | Gorman |
| 2004/0085215 A1 | 5/2004 | Moberg |
| 2004/0092873 A1 | 5/2004 | Moberg |
| 2004/0116866 A1 | 6/2004 | Gorman |
| 2004/0127857 A1 | 7/2004 | Shemesh |
| 2004/0158172 A1 | 8/2004 | Hancock |
| 2004/0186419 A1 | 9/2004 | Cho |
| 2004/0186424 A1 | 9/2004 | Hjertman |
| 2004/0260233 A1 | 12/2004 | Garibotto |
| 2005/0033234 A1 | 2/2005 | Sadowski |
| 2005/0049553 A1 | 3/2005 | Triplett |
| 2005/0065466 A1 | 3/2005 | Vedrine |
| 2005/0065472 A1 | 3/2005 | Cindrich |
| 2005/0070845 A1 | 3/2005 | Faries |
| 2005/0071487 A1 | 3/2005 | Lu |
| 2005/0075608 A1 | 4/2005 | Holdgate |
| 2005/0113761 A1 | 5/2005 | Faust |
| 2005/0159706 A1 | 7/2005 | Wilkinson |
| 2005/0171476 A1 | 8/2005 | Judson |
| 2005/0171512 A1 | 8/2005 | Flaherty |
| 2005/0177136 A1 | 8/2005 | Miller |
| 2005/0197650 A1 | 9/2005 | Sugimoto |
| 2005/0203461 A1 | 9/2005 | Flaherty |
| 2005/0238507 A1 | 10/2005 | DiIanni |
| 2005/0283114 A1 | 12/2005 | Bresina |
| 2006/0013716 A1 | 1/2006 | Nason |
| 2006/0030816 A1 | 2/2006 | Zubry |
| 2006/0095014 A1 | 5/2006 | Ethelfeld |
| 2006/0122577 A1 | 6/2006 | Poulsen |
| 2006/0173406 A1 | 8/2006 | Hayes |
| 2006/0173408 A1 | 8/2006 | Wyrick |
| 2006/0173410 A1 | 8/2006 | Moberg |
| 2006/0173439 A1 | 8/2006 | Thorne |
| 2006/0184154 A1 | 8/2006 | Moberg |
| 2006/0195029 A1 | 8/2006 | Shults |
| 2006/0211982 A1 | 9/2006 | Prestrelski |
| 2006/0229569 A1 | 10/2006 | Lavi |
| 2006/0253086 A1 | 11/2006 | Moberg |
| 2006/0264831 A1 | 11/2006 | Skwarek |
| 2006/0264889 A1 | 11/2006 | Moberg |
| 2006/0264890 A1 | 11/2006 | Moberg |
| 2006/0264894 A1 | 11/2006 | Moberg |
| 2006/0270987 A1 | 11/2006 | Peter |
| 2006/0283465 A1 | 12/2006 | Nickel |
| 2006/0293722 A1 | 12/2006 | Slatkine |
| 2007/0016381 A1 | 1/2007 | Kamath |
| 2007/0021733 A1 | 1/2007 | Hansen |
| 2007/0049865 A1 | 3/2007 | Radmer |
| 2007/0073228 A1 | 3/2007 | Mernoe |
| 2007/0106218 A1 | 5/2007 | Yodfat |
| 2007/0118405 A1 | 5/2007 | Campbell |
| 2007/0123819 A1 | 5/2007 | Mernoe |
| 2007/0129688 A1 | 6/2007 | Scheurer |
| 2007/0149926 A1 | 6/2007 | Moberg |
| 2007/0167912 A1 | 7/2007 | Causey |
| 2007/0185449 A1 | 8/2007 | Mernoe |
| 2007/0191770 A1 | 8/2007 | Moberg |
| 2007/0197968 A1 | 8/2007 | Pongpairochana |
| 2007/0203454 A1 | 8/2007 | Shermer |
| 2007/0219480 A1 | 9/2007 | Kamen |
| 2007/0233038 A1 | 10/2007 | Pruitt |
| 2007/0239116 A1 | 10/2007 | Follman |
| 2007/0282269 A1 | 12/2007 | Carter |
| 2008/0021439 A1 | 1/2008 | Brittingham |
| 2008/0033367 A1 | 2/2008 | Haury |
| 2008/0033369 A1 | 2/2008 | Kohlbrenner |
| 2008/0033393 A1 | 2/2008 | Edwards |
| 2008/0051710 A1 | 2/2008 | Moberg |
| 2008/0051711 A1 | 2/2008 | Mounce |
| 2008/0051727 A1 | 2/2008 | Moberg |
| 2008/0051730 A1 | 2/2008 | Bikovsky |
| 2008/0059133 A1 | 3/2008 | Edwards |
| 2008/0097381 A1 | 4/2008 | Moberg |
| 2008/0108951 A1 | 5/2008 | Jerde |
| 2008/0108953 A1 | 5/2008 | Moser |
| 2008/0125700 A1 | 5/2008 | Moberg |
| 2008/0140006 A1 | 6/2008 | Eskuri |
| 2008/0140018 A1 | 6/2008 | Enggaard |
| 2008/0147004 A1 | 6/2008 | Mann |
| 2008/0156476 A1 | 7/2008 | Smisson |
| 2008/0167641 A1 | 7/2008 | Hansen |
| 2008/0188813 A1 | 8/2008 | Miller |
| 2008/0195049 A1 | 8/2008 | Thalmann |
| 2008/0208138 A1 | 8/2008 | Lim |
| 2008/0215006 A1 | 9/2008 | Thorkild |
| 2008/0215015 A1 | 9/2008 | Cindrich |
| 2008/0221522 A1 | 9/2008 | Moberg |
| 2008/0221523 A1 | 9/2008 | Moberg |
| 2008/0234627 A1 | 9/2008 | Dent |
| 2008/0243087 A1 | 10/2008 | Enggaard |
| 2008/0249473 A1 | 10/2008 | Rutti |
| 2008/0255516 A1 | 10/2008 | Yodfat |
| 2008/0262436 A1 | 10/2008 | Olson |
| 2008/0269687 A1 | 10/2008 | Chong |
| 2008/0269689 A1 | 10/2008 | Edwards |
| 2008/0269723 A1 | 10/2008 | Mastrototaro |
| 2008/0274630 A1 | 11/2008 | Shelton |
| 2008/0275407 A1 | 11/2008 | Scheurer |
| 2008/0281270 A1 | 11/2008 | Cross |
| 2008/0294143 A1 | 11/2008 | Tanaka |
| 2008/0306449 A1 | 12/2008 | Kristensen |
| 2008/0312601 A1 | 12/2008 | Cane |
| 2008/0312604 A1 | 12/2008 | Boesen |
| 2008/0319416 A1 | 12/2008 | Yodfat |
| 2009/0024112 A1 | 1/2009 | Edwards |
| 2009/0030366 A1 | 1/2009 | Hochman |
| 2009/0041805 A1 | 2/2009 | Walker |
| 2009/0043253 A1 | 2/2009 | Podaima |
| 2009/0048347 A1 | 2/2009 | Cohen |
| 2009/0054750 A1 | 2/2009 | Jennewine |
| 2009/0054852 A1 | 2/2009 | Takano |
| 2009/0062767 A1 | 3/2009 | Van Antwerp |
| 2009/0069784 A1 | 3/2009 | Estes |

(56) References Cited

U.S. PATENT DOCUMENTS

| | | |
|---|---|---|
| 2009/0076360 A1 | 3/2009 | Brister |
| 2009/0076453 A1 | 3/2009 | Mejlhede |
| 2009/0088694 A1 | 4/2009 | Carter |
| 2009/0088731 A1 | 4/2009 | Campbell |
| 2009/0093792 A1 | 4/2009 | Gross |
| 2009/0093793 A1 | 4/2009 | Gross |
| 2009/0105650 A1 | 4/2009 | Wiegel |
| 2009/0124977 A1 | 5/2009 | Jensen |
| 2009/0131860 A1 | 5/2009 | Nielsen |
| 2009/0139724 A1 | 6/2009 | Gray |
| 2009/0143730 A1 | 6/2009 | De Polo |
| 2009/0143735 A1 | 6/2009 | De Polo |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0216103 A1 | 8/2009 | Brister |
| 2009/0216194 A1 | 8/2009 | Elgaard |
| 2009/0234319 A1 | 9/2009 | Marksteiner |
| 2009/0240240 A1 | 9/2009 | Hines |
| 2009/0243234 A1 | 10/2009 | Sharifi |
| 2009/0253973 A1 | 10/2009 | Bashan |
| 2009/0259176 A1 | 10/2009 | Yairi |
| 2009/0281585 A1 | 11/2009 | Katzman |
| 2009/0299290 A1 | 12/2009 | Moberg |
| 2009/0299397 A1 | 12/2009 | Ruan |
| 2009/0326459 A1 | 12/2009 | Shipway |
| 2009/0326509 A1 | 12/2009 | Muse |
| 2010/0030156 A1 | 2/2010 | Beebe |
| 2010/0030198 A1 | 2/2010 | Beebe |
| 2010/0037680 A1 | 2/2010 | Moberg |
| 2010/0049128 A1 | 2/2010 | McKenzie |
| 2010/0049144 A1 | 2/2010 | McConnell |
| 2010/0057057 A1 | 3/2010 | Hayter |
| 2010/0076412 A1 | 3/2010 | Rush |
| 2010/0081993 A1 | 4/2010 | O'Connor |
| 2010/0094255 A1 | 4/2010 | Nycz |
| 2010/0100076 A1 | 4/2010 | Rush |
| 2010/0100077 A1 | 4/2010 | Rush |
| 2010/0106098 A1 | 4/2010 | Atterbury |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat |
| 2010/0145305 A1 | 6/2010 | Alon |
| 2010/0152658 A1 | 6/2010 | Hanson |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn |
| 2010/0204657 A1 | 8/2010 | Yodfat |
| 2010/0211005 A1 | 8/2010 | Edwards |
| 2010/0211011 A1 | 8/2010 | Haar |
| 2010/0217192 A1 | 8/2010 | Moberg |
| 2010/0217193 A1 | 8/2010 | Moberg |
| 2010/0234767 A1 | 9/2010 | Sarstedt |
| 2010/0234805 A1 | 9/2010 | Kaufmann |
| 2010/0234830 A1 | 9/2010 | Straessler |
| 2010/0241065 A1 | 9/2010 | Moberg |
| 2010/0264931 A1 | 10/2010 | Lindegger |
| 2010/0274112 A1 | 10/2010 | Hoss |
| 2010/0274192 A1 | 10/2010 | Mernoe |
| 2010/0274202 A1 | 10/2010 | Hyde |
| 2010/0276411 A1 | 11/2010 | Hansen |
| 2010/0280499 A1 | 11/2010 | Yodfat |
| 2010/0331826 A1 | 12/2010 | Field |
| 2011/0034900 A1 | 2/2011 | Yodfat |
| 2011/0054399 A1 | 3/2011 | Chong |
| 2011/0054400 A1 | 3/2011 | Chong |
| 2011/0060284 A1 | 3/2011 | Harr |
| 2011/0066131 A1 | 3/2011 | Cabiri |
| 2011/0092917 A1 | 4/2011 | Wei |
| 2011/0119033 A1 | 5/2011 | Moberg |
| 2011/0125056 A1 | 5/2011 | Merchant |
| 2011/0137239 A1 | 6/2011 | Debelser |
| 2011/0137247 A1 | 6/2011 | Mesa et al. |
| 2011/0144584 A1 | 6/2011 | Wozencroft |
| 2011/0152780 A1 | 6/2011 | Villette et al. |
| 2011/0160654 A1 | 6/2011 | Hanson |
| 2011/0160655 A1 | 6/2011 | Hanson |
| 2011/0160666 A1 | 6/2011 | Hanson |
| 2011/0160669 A1 | 6/2011 | Gyrn |
| 2011/0172645 A1 | 7/2011 | Moga |
| 2011/0172745 A1 | 7/2011 | Na |
| 2011/0178463 A1 | 7/2011 | Cabiri |
| 2011/0178472 A1 | 7/2011 | Cabiri |
| 2011/0184342 A1 | 7/2011 | Pesach |
| 2011/0201998 A1 | 8/2011 | Pongpairochana |
| 2011/0224614 A1 | 9/2011 | Moberg |
| 2011/0238031 A1 | 9/2011 | Adair |
| 2011/0245773 A1 | 10/2011 | Estes |
| 2011/0264383 A1 | 10/2011 | Moberg |
| 2011/0270160 A1 | 11/2011 | Mernoe |
| 2011/0282282 A1 | 11/2011 | Lorenzen |
| 2011/0282296 A1 | 11/2011 | Harms |
| 2011/0295205 A1 | 12/2011 | Kaufmann |
| 2011/0313238 A1 | 12/2011 | Reichenbach |
| 2011/0313351 A1 | 12/2011 | Kamen |
| 2011/0319861 A1 | 12/2011 | Wilk |
| 2011/0319919 A1 | 12/2011 | Curry |
| 2012/0004602 A1 | 1/2012 | Hanson |
| 2012/0010594 A1 | 1/2012 | Holt |
| 2012/0022344 A1 | 1/2012 | Kube |
| 2012/0022499 A1 | 1/2012 | Anderson |
| 2012/0025995 A1 | 2/2012 | Moberg |
| 2012/0029431 A1 | 2/2012 | Charles |
| 2012/0035546 A1 | 2/2012 | Cabiri |
| 2012/0041364 A1 | 2/2012 | Smith |
| 2012/0041370 A1 | 2/2012 | Moberg |
| 2012/0041414 A1 | 2/2012 | Estes |
| 2012/0059332 A1 | 3/2012 | Woehr |
| 2012/0071819 A1 | 3/2012 | Brueggemann et al. |
| 2012/0071828 A1 | 3/2012 | Tojo |
| 2012/0096953 A1 | 4/2012 | Bente, IV |
| 2012/0096954 A1 | 4/2012 | Vazquez |
| 2012/0101436 A1 | 4/2012 | Bazargan |
| 2012/0108933 A1 | 5/2012 | Liang |
| 2012/0116311 A1 | 5/2012 | Brueggemann |
| 2012/0129362 A1 | 5/2012 | Hampo |
| 2012/0143136 A1 | 6/2012 | Constantineau |
| 2012/0160033 A1 | 6/2012 | Kow |
| 2012/0165733 A1 | 6/2012 | Bazargan |
| 2012/0165780 A1 | 6/2012 | Bazargan |
| 2012/0172804 A1 | 7/2012 | Plumptre |
| 2012/0215169 A1 | 8/2012 | Moberg |
| 2012/0215199 A1 | 8/2012 | Moberg |
| 2012/0226234 A1 | 9/2012 | Bazargan |
| 2012/0259282 A1 | 10/2012 | Alderete, Jr. |
| 2012/0310153 A1 | 12/2012 | Moberg |
| 2013/0012875 A1 | 1/2013 | Gross |
| 2013/0030378 A1 | 1/2013 | Jugl et al. |
| 2013/0041346 A1 | 2/2013 | Alon |
| 2013/0060233 A1 | 3/2013 | O'Connor |
| 2013/0068319 A1 | 3/2013 | Plumptre |
| 2013/0085457 A1 | 4/2013 | Schiff |
| 2013/0089992 A1 | 4/2013 | Yang |
| 2013/0096509 A1 | 4/2013 | Avery |
| 2013/0110049 A1 | 5/2013 | Cronenberg |
| 2013/0133438 A1 | 5/2013 | Kow |
| 2013/0175192 A1 | 7/2013 | Iio |
| 2013/0190691 A1 | 7/2013 | Cabiri |
| 2013/0211330 A1 | 8/2013 | Pedersen |
| 2013/0218089 A1 | 8/2013 | Davies |
| 2013/0218092 A1 | 8/2013 | Davies |
| 2013/0226098 A1 | 8/2013 | Tokumoto |
| 2013/0237953 A1 | 9/2013 | Kow |
| 2013/0245595 A1 | 9/2013 | Kow |
| 2013/0245596 A1 | 9/2013 | Cabiri |
| 2013/0245604 A1 | 9/2013 | Kouyoumjian |
| 2013/0253419 A1 | 9/2013 | Favreau |
| 2013/0253420 A1 | 9/2013 | Favreau |
| 2013/0253421 A1 | 9/2013 | Favreau |
| 2013/0253432 A1* | 9/2013 | Avery .................. A61M 5/5086 29/428 |

(56) References Cited

U.S. PATENT DOCUMENTS

| | | |
|---|---|---|
| 2013/0253434 A1 | 9/2013 | Cabiri |
| 2013/0253472 A1 | 9/2013 | Cabiri |
| 2013/0281936 A1 | 10/2013 | Kemp |
| 2013/0296785 A1 | 11/2013 | Cabiri |
| 2013/0296792 A1 | 11/2013 | Cabiri |
| 2013/0296799 A1 | 11/2013 | Degtiar |
| 2013/0304021 A1 | 11/2013 | Cabiri |
| 2013/0310753 A1 | 11/2013 | Cabiri |
| 2013/0323699 A1 | 12/2013 | Edwards |
| 2013/0331791 A1 | 12/2013 | Gross |
| 2014/0055073 A1 | 2/2014 | Favreau |
| 2014/0055076 A1 | 2/2014 | Favreau |
| 2014/0058349 A1 | 2/2014 | Bazargan |
| 2014/0074041 A1 | 3/2014 | Pedersen |
| 2014/0083517 A1 | 3/2014 | Moia |
| 2014/0094755 A1 | 4/2014 | Bazargan |
| 2014/0128807 A1 | 5/2014 | Moberg |
| 2014/0128815 A1 | 5/2014 | Cabiri |
| 2014/0128835 A1 | 5/2014 | Moberg |
| 2014/0135692 A1 | 5/2014 | Alderete, Jr. |
| 2014/0135694 A1 | 5/2014 | Moberg |
| 2014/0142499 A1 | 5/2014 | Moberg |
| 2014/0148784 A1 | 5/2014 | Anderson |
| 2014/0148785 A1 | 5/2014 | Moberg |
| 2014/0155827 A1 | 6/2014 | Ostrander |
| 2014/0163522 A1 | 6/2014 | Alderete, Jr. |
| 2014/0171881 A1 | 6/2014 | Cabiri |
| 2014/0174223 A1 | 6/2014 | Gross |
| 2014/0188073 A1 | 7/2014 | Cabiri |
| 2014/0194819 A1 | 7/2014 | Maule |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0210631 A1 | 7/2014 | Zavis |
| 2014/0213975 A1 | 7/2014 | Clemente |
| 2014/0236087 A1 | 8/2014 | Alderete, Jr. |
| 2014/0261758 A1 | 9/2014 | Wlodarczyk |
| 2014/0288511 A1 | 9/2014 | Tan-Malecki |
| 2014/0322935 A1 | 10/2014 | Filman |
| 2014/0330240 A1 | 11/2014 | Cabiri |
| 2014/0343503 A1 | 11/2014 | Holmqvist |
| 2015/0011965 A1 | 1/2015 | Cabiri |
| 2015/0011976 A1 | 1/2015 | Vouillamoz |
| 2015/0032084 A1 | 1/2015 | Cabiri |
| 2015/0057613 A1 | 2/2015 | Clemente |
| 2015/0061389 A1 | 3/2015 | Song |
| 2015/0080810 A1 | 3/2015 | Henderson |
| 2015/0119797 A1 | 4/2015 | Cabiri |
| 2015/0165121 A1 | 6/2015 | Murakami |
| 2015/0180146 A1 | 6/2015 | Filman |
| 2015/0224253 A1 | 8/2015 | Cabiri |
| 2015/0224258 A1 | 8/2015 | Holtwick |
| 2015/0320990 A1 | 11/2015 | Burton |
| 2015/0374926 A1 | 12/2015 | Gross |
| 2016/0015910 A1 | 1/2016 | Mukai |
| 2016/0030665 A1 | 2/2016 | Cabiri |
| 2016/0038691 A1 | 2/2016 | Mounce |
| 2016/0051765 A1 | 2/2016 | Morris |
| 2016/0051767 A1 | 2/2016 | Higgins |
| 2016/0058941 A1 | 3/2016 | Wu |
| 2016/0106929 A1 | 4/2016 | Fournier |
| 2016/0136353 A1 | 5/2016 | Adams |
| 2016/0158436 A1 | 6/2016 | Yang |
| 2016/0175539 A1 | 6/2016 | Riedel |
| 2016/0199590 A1 | 7/2016 | Schabbach |
| 2016/0199592 A1 | 7/2016 | Eggert |
| 2016/0213840 A1 | 7/2016 | Schabbach |
| 2016/0228644 A1 | 8/2016 | Cabiri |
| 2016/0256352 A1 | 9/2016 | Bar-El |
| 2016/0259913 A1 | 9/2016 | Yu |
| 2016/0296716 A1 | 10/2016 | Cabiri |
| 2016/0303324 A1 | 10/2016 | Cabiri |
| 2016/0317736 A1 | 11/2016 | Schabbach |
| 2016/0317737 A1 | 11/2016 | Schabbach |
| 2016/0346478 A1 | 12/2016 | Bar-El |
| 2016/0366946 A1 | 12/2016 | Murison |
| 2017/0007774 A1 | 1/2017 | Brockmeier |
| 2017/0028132 A1 | 2/2017 | Cronenberg |
| 2017/0043092 A1 | 2/2017 | Murakami |
| 2017/0080158 A1 | 3/2017 | Cabiri |
| 2017/0106138 A1 | 4/2017 | Cabiri |
| 2017/0165414 A1 | 6/2017 | Schieve |
| 2017/0182303 A1 | 6/2017 | Tallarida |
| 2017/0224915 A1 | 8/2017 | Destefano |
| 2017/0224934 A1 | 8/2017 | Shultz |
| 2017/0281859 A1 | 10/2017 | Agard |
| 2017/0312450 A1 | 11/2017 | Gross |
| 2017/0348478 A1 | 12/2017 | Tobescu |
| 2017/0354781 A1 | 12/2017 | Cronenberg |
| 2017/0354782 A1 | 12/2017 | Quinn |
| 2017/0354783 A1 | 12/2017 | Gazeley |
| 2017/0354785 A1 | 12/2017 | Gazeley |
| 2017/0354788 A1 | 12/2017 | Quinn |
| 2018/0001073 A1 | 1/2018 | Clemente |
| 2018/0008769 A1 | 1/2018 | O'Connor |
| 2018/0021508 A1 | 1/2018 | Destefano |
| 2018/0028747 A1 | 2/2018 | Hanson |
| 2018/0043091 A1 | 2/2018 | Agard |
| 2018/0055995 A1 | 3/2018 | Hanson |
| 2018/0152281 A1 | 5/2018 | Zigelboim |
| 2018/0154081 A1 | 6/2018 | Bar-El |
| 2018/0236173 A1 | 8/2018 | McCaffrey |
| 2019/0046720 A1 | 2/2019 | Kamen |
| 2019/0091404 A1 | 3/2019 | Nazzaro |
| 2019/0117880 A1 | 4/2019 | Hirschel |
| 2019/0117902 A1 | 4/2019 | Hodgson |
| 2019/0151565 A1 | 5/2019 | Groetzbach |
| 2019/0201634 A1 | 7/2019 | Newton |
| 2019/0209787 A1 | 7/2019 | Bendek |
| 2019/0336701 A1 | 11/2019 | Moore |
| 2019/0351149 A1 | 11/2019 | Ward |
| 2019/0366012 A1 | 12/2019 | Gross |
| 2019/0374727 A1 | 12/2019 | Dugand |
| 2020/0038598 A1 | 2/2020 | Chu |
| 2020/0046910 A1 | 2/2020 | Maxfield |
| 2020/0054823 A1 | 2/2020 | Baier |
| 2020/0085695 A1 | 3/2020 | O'Keefe |
| 2020/0114068 A1 | 4/2020 | Schmidlin |
| 2020/0121909 A1 | 4/2020 | Shaked |
| 2020/0222623 A1 | 7/2020 | Roberts |
| 2020/0222638 A1 | 7/2020 | Lafever |
| 2020/0238012 A1 | 7/2020 | Bar-El |
| 2020/0397977 A1 | 12/2020 | Keitzmann |

FOREIGN PATENT DOCUMENTS

| | | |
|---|---|---|
| CN | 1408443 A | 4/2003 |
| CN | 1636605 A | 7/2005 |
| CN | 1747683 A | 3/2006 |
| CN | 1756573 A | 4/2006 |
| CN | 1863566 A | 11/2006 |
| CN | 1929884 A | 3/2007 |
| CN | 101001661 A | 7/2007 |
| CN | 101027094 | 8/2007 |
| CN | 101090749 A | 12/2007 |
| CN | 101239205 A | 8/2008 |
| CN | 101262898 | 9/2008 |
| CN | 101460207 A | 6/2009 |
| CN | 101528286 | 9/2009 |
| CN | 101631585 A | 1/2010 |
| CN | 101687083 A | 3/2010 |
| CN | 101868273 A | 10/2010 |
| CN | 101970033 A | 2/2011 |
| CN | 201941304 U | 8/2011 |
| CN | 102186733 A | 9/2011 |
| CN | 102256657 A | 11/2011 |
| CN | 102271735 | 12/2011 |
| CN | 102378638 A | 3/2012 |
| CN | 102497909 | 6/2012 |
| CN | 102753233 | 10/2012 |
| CN | 103118723 | 5/2013 |
| CN | 103269730 | 8/2013 |
| CN | 103687636 | 3/2014 |

(56) References Cited

FOREIGN PATENT DOCUMENTS

| | | |
|---|---|---|
| CN | 103727021 | 4/2014 |
| CN | 103874460 A | 6/2014 |
| CN | 104136059 A | 11/2014 |
| CN | 104271043 | 1/2015 |
| CN | 104321093 | 1/2015 |
| CN | 104853787 | 8/2015 |
| CN | 104870049 | 8/2015 |
| CN | 105188636 A | 12/2015 |
| CN | 105263562 | 1/2016 |
| CN | 105492039 | 4/2016 |
| CN | 105517593 A | 4/2016 |
| CN | 205287099 U | 6/2016 |
| CN | 105899248 | 8/2016 |
| CN | 106029122 A | 10/2016 |
| CN | 106029127 A | 10/2016 |
| CN | 106029128 | 10/2016 |
| CN | 106456892 A | 2/2017 |
| CN | 106470719 | 3/2017 |
| DE | 1064693 B | 9/1959 |
| EP | 0017412 A1 | 10/1980 |
| EP | 0222656 A1 | 5/1987 |
| EP | 0401179 A1 | 12/1990 |
| EP | 0744975 A1 | 12/1996 |
| EP | 1530979 A1 | 5/2005 |
| EP | 1666080 A1 | 6/2006 |
| EP | 2060606 A1 | 5/2009 |
| EP | 2231234 | 9/2010 |
| EP | 2345441 A1 | 7/2011 |
| EP | 2361648 A1 | 8/2011 |
| EP | 2364741 A1 | 9/2011 |
| EP | 2459251 | 6/2012 |
| EP | 2498589 A1 | 9/2012 |
| EP | 2529776 A1 | 12/2012 |
| EP | 2698180 A1 | 2/2014 |
| EP | 2727617 A1 | 5/2014 |
| EP | 2729203 | 5/2014 |
| EP | 2862588 A1 | 4/2015 |
| EP | 2873431 | 5/2015 |
| EP | 2454483 B1 | 8/2015 |
| EP | 2932993 A1 | 10/2015 |
| EP | 2944340 | 11/2015 |
| EP | 2285360 | 4/2016 |
| EP | 3031486 A1 | 6/2016 |
| EP | 3100754 A1 | 12/2016 |
| EP | 3226944 | 10/2017 |
| EP | 3260149 A1 * | 12/2017 ........ A61M 5/14248 |
| EP | 3409312 | 12/2018 |
| EP | 3458131 | 3/2019 |
| EP | 2244765 | 8/2019 |
| EP | 3552642 | 10/2019 |
| EP | 3618903 | 3/2020 |
| EP | 3626291 | 3/2020 |
| EP | 3659652 | 6/2020 |
| EP | 3501584 | 9/2020 |
| FR | 2905273 A1 | 3/2008 |
| GB | 2552340 | 1/2018 |
| JP | H09505758 A | 6/1997 |
| JP | 2001512992 A | 8/2001 |
| JP | 2002500525 | 1/2002 |
| JP | 2002505601 A | 2/2002 |
| JP | 2002528676 A | 9/2002 |
| JP | 2003501157 A | 1/2003 |
| JP | 2003527138 A | 9/2003 |
| JP | 2003534061 A | 11/2003 |
| JP | 2004501721 A | 1/2004 |
| JP | 2004512100 A | 4/2004 |
| JP | 2005523127 A | 8/2005 |
| JP | 2005270629 A | 10/2005 |
| JP | 2007509661 A | 4/2007 |
| JP | 2008043761 | 2/2008 |
| JP | 2008508950 | 3/2008 |
| JP | 2008534131 A | 8/2008 |
| JP | 2008220961 A | 9/2008 |
| JP | 2009502273 A | 1/2009 |
| JP | 4305704 B2 | 7/2009 |
| JP | 2011519712 | 7/2011 |
| JP | 2012501771 A | 1/2012 |
| JP | 2012050847 | 3/2012 |
| JP | 2012115675 | 6/2012 |
| JP | 2012516737 | 7/2012 |
| JP | 2013504405 | 2/2013 |
| JP | 2013521084 A | 6/2013 |
| JP | 2013542807 | 11/2013 |
| JP | 2014510571 | 5/2014 |
| JP | 2014516667 A | 7/2014 |
| JP | 2014516701 | 7/2014 |
| JP | 2014516702 A | 7/2014 |
| JP | 2015536696 A | 12/2015 |
| JP | 2016507290 A | 3/2016 |
| JP | 2016513509 | 5/2016 |
| JP | 2016516553 | 6/2016 |
| JP | 2016518879 | 6/2016 |
| JP | 2016523123 | 8/2016 |
| JP | 2017510419 | 4/2017 |
| JP | 2017086630 | 5/2017 |
| JP | 2017513623 | 6/2017 |
| KR | 20140000766 U | 2/2014 |
| WO | 8911302 A1 | 11/1989 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9521645 A1 | 8/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9721457 A1 | 6/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |
| WO | 02072182 A1 | 9/2002 |
| WO | 0390833 A1 | 11/2003 |
| WO | 2004032990 A2 | 4/2004 |
| WO | 2004069302 A2 | 8/2004 |
| WO | 2004105841 A1 | 12/2004 |
| WO | 2005018703 A2 | 3/2005 |
| WO | 2005037350 A2 | 4/2005 |
| WO | 2005077441 A2 | 8/2005 |
| WO | 2006037434 A1 | 4/2006 |
| WO | 2006069380 A1 | 6/2006 |
| WO | 2006102676 A1 | 9/2006 |
| WO | 2006104806 A2 | 10/2006 |
| WO | 2006108809 A1 | 10/2006 |
| WO | 2007051563 A1 | 5/2007 |
| WO | 2007056504 A1 | 5/2007 |
| WO | 2007092618 A2 | 8/2007 |
| WO | 2007130868 A1 | 11/2007 |
| WO | 2008001377 A2 | 1/2008 |
| WO | 2008014908 A1 | 2/2008 |
| WO | 2008024810 A2 | 2/2008 |
| WO | 2008024814 A2 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2008129549 A1 | 10/2008 |
| WO | 2009044401 A2 | 4/2009 |
| WO | 2009046989 A2 | 4/2009 |
| WO | 2009081262 A1 | 7/2009 |
| WO | 2009088956 | 7/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2011014704 A2 | 2/2011 |
| WO | 2011034799 A1 | 3/2011 |

(56) References Cited

FOREIGN PATENT DOCUMENTS

| | | |
|---|---|---|
| WO | 2011075105 A1 | 6/2011 |
| WO | 2011090955 A1 | 7/2011 |
| WO | 2011090956 A2 | 7/2011 |
| WO | 2011104711 A1 | 9/2011 |
| WO | 2011113806 A1 | 9/2011 |
| WO | 2011156373 A1 | 12/2011 |
| WO | 2012013140 | 2/2012 |
| WO | 2012032411 A2 | 3/2012 |
| WO | 2012040528 A1 | 3/2012 |
| WO | 2012064258 A1 | 5/2012 |
| WO | 2012160157 A1 | 11/2012 |
| WO | 2012160160 A1 | 11/2012 |
| WO | 2013036602 A1 | 3/2013 |
| WO | 2013115843 A1 | 8/2013 |
| WO | 2013148270 A2 | 10/2013 |
| WO | 2013148435 A1 | 10/2013 |
| WO | 2013173092 A1 | 11/2013 |
| WO | 2014052676 A1 | 4/2014 |
| WO | 2014070453 A1 | 5/2014 |
| WO | 2014107408 A1 | 7/2014 |
| WO | 2014111332 A1 | 7/2014 |
| WO | 2014144096 | 9/2014 |
| WO | 2014159017 A1 | 10/2014 |
| WO | 2014179210 A1 | 11/2014 |
| WO | 2014179774 A1 | 11/2014 |
| WO | 2015007857 | 1/2015 |
| WO | 2015018787 A1 | 2/2015 |
| WO | 2015032745 A1 | 3/2015 |
| WO | 2015044561 | 4/2015 |
| WO | 2015061389 A1 | 4/2015 |
| WO | 2015070914 A1 | 5/2015 |
| WO | 2015164649 | 10/2015 |
| WO | 2016033496 | 3/2016 |
| WO | 2016033507 A2 | 3/2016 |
| WO | 2016089864 | 6/2016 |
| WO | 2016113409 | 7/2016 |
| WO | 2016196934 | 12/2016 |
| WO | 2017004315 | 1/2017 |
| WO | 2017062931 | 4/2017 |
| WO | 2017064483 | 4/2017 |
| WO | 2017089266 | 6/2017 |
| WO | 2017090019 A2 | 6/2017 |
| WO | 2017127215 A1 | 7/2017 |
| WO | 2017210448 | 12/2017 |
| WO | 2018018165 | 2/2018 |
| WO | 2018018167 | 2/2018 |
| WO | 2018060023 | 4/2018 |
| WO | 2018070978 A1 | 4/2018 |
| WO | 2018096231 | 5/2018 |
| WO | 2018131046 | 7/2018 |
| WO | 2018222521 A1 | 12/2018 |
| WO | 2019074788 | 4/2019 |
| WO | 2019091626 | 5/2019 |
| WO | 2019101613 | 5/2019 |
| WO | 2019123073 | 6/2019 |
| WO | 2019197381 | 10/2019 |
| WO | 2020070260 | 4/2020 |

OTHER PUBLICATIONS

Int'l Preliminary Report on Patentability dated Jun. 23, 2020 in Int'l Application No. PCT/US2018/066660.
Christoph Kapitza, M.D.; Basal-Prandial Insulin Delivery in Type 2 Diabetes Mellitusvia the V-Go™; Jan. 2008; Diabetes Tech. Society; vol. 2, Issue 1; (Year: 2008).
Copaxone®, Innovative Drugs, Teva Pharmaceuticals, downloaded from webpage: http://tevapharm.com/copaxone/, Download date: Jan. 2009, original posting date: unknown, 2 pages.
Daikyo Crystal Zenith® polymer, Manufactured by Daikyo Seiko, Ltd. (Jun. 25, 2008). 2 pages.
Extended European Search Report dated Aug. 5, 2020 in European Application No. 18780556.9.
Extended European Search Report dated Aug. 7, 2014 in EP Application No. 1417477.4. 7 pages.
Extended European Search Report dated Feb. 23, 2015 in EP Application No. 14166596.8. 6 pages.
Extended European Search Report dated Feb. 23, 2015 in EP Application No. 14166591.9. 6 pages.
Extended European Search Report dated Mar. 27, 2014 in EP Application No. 14154717.4. 6 pages.
Int'l Preliminary Report of Patentability dated Feb. 11, 2020 in Int'l Application No. PCT/US2018/045506.
Int'l Preliminary Report on Patentability dated Apr. 7, 2010 in Int'l Application No. PCT/IL2008/001312.
Int'l Preliminary Report on Patentability dated Aug. 14, 2014 in Int'l Application No. PCT/US2012/050696.
Int'l Preliminary Report on Patentability dated Aug. 2, 2012 in Int'l Application No. PCT/US2011/021604.
Int'l Preliminary Report on Patentability dated Dec. 5, 2017 in In'tl Application No. PCT/US2016/035720.
Int'l Preliminary Report on Patentability dated Feb. 7, 2013 in Int'l Application No. PCT/US2011/021605.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Int'l Preliminary Report on Patentability dated Feb. 11, 20 in Int'l Application No. PCT/US2018/045004.
Int'l Preliminary Report on Patentability dated Feb. 26, 2020 in Int'l Application No. PCT/IB2018/001164.
Int'l Preliminary Reporton Patentability dated Dec. 4, 2019 in Int'l Application No. PCT/US2018/045114.
Int'l Preliminary Reporton Patentability dated Oct. 28, 2019 issued in Int'l Application No. PCT/US2018/044993.
Int'l Search Report and Written Opinion dated Apr. 3, 2014 in Int'l Application No. PCT/US2013/078040.
Int'l Search Report and Written Opinion dated Apr. 5, 2013 in Int'l Application No. PCT/US2012/050696.
Int'l Search Report and Written Opinion dated Aug. 12, 2016 in Int'l Application No. PCT/US2016/035720.
Int'l Search Report and Written Opinion dated Aug. 28, 2014 in Int'l Application No. PCT/US2014/035662.
Int'l Search Report and Written Opinion dated Aug. 5, 2013 in Int'l Application No. PCT/US2013/033118.
Int'l Search Report and Written Opinion dated Jan. 12, 2011 in Int'l Application No. PCT/US2010/048556; Written Opinion.
Int'l Search Report and Written Opinion dated Jan. 7, 2014 in Int'l Application No. PCT/US2013/065211.
Int'l Search Report and Written Opinion dated Jul. 12, 2018 in Int'l Application No. PCT/US2018/026556.
Int'l Search Report and Written Opinion dated Jul. 31, 2014 in Int'l Application No. PCT/US2014/033598.
Int'l Search Report and Written Opinion dated Jun. 30, 2014 in Int'l Application No. PCT/US2013/031598.
Int'l Search Report and Written Opinion dated May 13, 2009 in Int'l Application No. PCT/IL2008/001312.
Int'l Search Report and Written Opinion dated Nov. 5, 2012 in Int'l Application No. PCT/US2012/039465.
Int'l Search Report and Written Opinion dated Oct. 23, 2018 in Int'l Application No. PCT/US2018/045114.
Int'l Search Report and Written Opinion dated Oct. 25, 2018 in Int'l Application No. PCT/US2018/044993.
Int'l Search Report and Written Opinion dated Oct. 26, 2018 in Int'l Application No. PCT/US2018/045506.
Int'l Search Report and Written Opinion dated Jan. 4, 2019 in Int'l Application No. PCT/US2018/045004.
Int'l Search Report and Written Opinion dated Jan. 4, 2019 in Int'l Application No. PCT/IB2018/001164.
Int'l Search Report dated Apr. 26, 2010 in Int'l Application No. PCT/US2009/069552.

(56) References Cited

OTHER PUBLICATIONS

Int'l Search Report dated Jun. 17, 2011 in Int'l Application No. PCT/US2011/021604.
Int'l Search Report dated Oct. 12, 2011 in Int'l Application No. PCT/US2011/021605.
Int'l Search Report dated Sep. 22, 2011 in Int'l Application No. PCT/IL 11/00368; Written Opinion.
International Preliminary Report on Patentability and Written Opinion dated Jul. 5, 2011 in International Application No. PCT/US2009/069552.
International Preliminary Report on Patentability dated Aug. 12, 2019 in International Application No. PCT/US2018/045084.
International Search Report and Written Opinion dated Dec. 19, 2018 in International Application No. PCT/US2018/045084.
International Search Report and Written Opinion dated Nov. 15, 2018 in International Appl. No. PCT/US2018/045149.
Notice of Allowance dated Aug. 24, 2015 in U.S. Appl. No. 29/479,307 by Norton.
Notice of Allowance dated Apr. 25, 2016 in U.S. Appl. No. 14/553,399 by Cabiri.
Notice of Allowance dated May 11, 2016 in U.S. Appl. No. 14/931,439 by Cabiri.
Office Action dated Apr. 19, 2016 in U.S. Appl. No. 14/372,384, by Cabiri.
Office Action dated Apr. 23, 2015 in JP Application No. 2012-550069.
Office Action dated Apr. 24, 2013 in CN Application No. 201080040968.7.
Office Action dated Apr. 5, 2010 in U.S. Appl. No. 12/244,666.
Office Action dated Apr. 5, 2010 in U.S. Appl. No. 12/244,688.
Office Action dated Aug. 13, 2015 in U.S. Appl. No. 14/553,399 by Cabiri.
Office Action dated Aug. 13, 2018 in IN Application No. 857/KOLNP/2012.
Office Action dated Aug. 15, 2013 in CN Application No. 200880117084.X.
Office Action dated Aug. 15, 2013 in U.S. Appl. No. 13/429,942 by Cabiri.
Office Action dated Aug. 26, 2014 in CN Application No. 201180006567.4.
Office Action dated Aug. 29, 2014 in JP Application No. 2012-550068.
Office Action dated Aug. 29, 2014 in JP Application No. 2012-550069.
Office Action dated Aug. 6, 2014 in EP Application No. 11 707 942.6.
Office Action dated Dec. 10, 2013 in CN Application No. 201180006567.4.
Office Action dated Dec. 12, 2013 in JP Application No. 2012-529808.
Office Action dated Dec. 29, 2016 in CN Application No. 201510695320.8.
Office Action dated Feb. 20, 2015 in U.S. Appl. No. 13/521, 181 by Cabiri.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2016 in U.S. Appl. No. 13/429,942 by Cabiri.
Office Action dated Feb. 4, 2014 in EP Application No. 11 707 942.6.
Office Action dated Jan. 15, 2016 in U.S. Appl. No. 13/472,112 by Cabiri.
Office Action dated Jan. 16, 2014 in U.S. Appl. No. 13/429,942 by Cabiri.
Office Action dated Jan. 28, 2015 in U.S. Appl. No. 13/429,942 by Cabiri.
Office Action dated Jan. 30, 2013 in CN Application No. 200880117084.X.
Office Action dated Jan. 4, 2016 in U.S. Appl. No. 13/892,905 by Cabiri.
Office Action dated Jan. 5, 2016 in U.S. Appl. No. 14/696,644 by Cabiri.
Office Action dated Jan. 8, 2014 in U.S. Appl. No. 13/521, 167 by Cabiri.
Office Action dated Jul. 13, 2011 in U.S. Appl. No. 12/559,563.
Office Action dated Jul. 14, 2020 in Japanese Application No. 2020-507100.
Office Action dated Jul. 2, 2012 in U.S. Appl. No. 13/272,555.
Office Action dated Jul. 29, 2013 in JP Application No. 2012-529808.
Office Action dated Jul. 29, 2016 in U.S. Appl. No. 14/696,644, by Cabiri.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jul. 7, 2016 in U.S. Appl. No. 13/892,905 by Cabiri.
Office Action dated Jun. 1, 2016 in CN Application No. 201380027455.6.
Office Action dated Jun. 16, 2021 in Chinese Office Action 201880065173.8.
Office Action dated Jun. 17, 2016 in CN Application No. 201280068544.0.
Office Action dated Mar. 2, 2021 in Japanese Application No. 2020-506901.
Office Action dated Jun. 3, 2014 in JP Application No. 2010-527595.
Office Action dated Jun. 4, 2015 in U.S. Appl. No. 13/667,739 by Cabiri.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 15, 2018 in U.S. Appl. No. 29/628,592 by Cabiri.
Office Action dated Mar. 17, 2020 in JP Application No. 2019-554804.
Office Action dated Mar. 23, 2015 in JP Application No. 2012-550068.
Office Action dated May 1, 2015 in U.S. Appl. No. 14/638,525 by Filman.
Office Action dated May 13, 2015 in CN Application No. 201380025566.3.
Office Action dated May 16, 2012 in U.S. Appl. No. 12/615,828.
Office Action dated May 17, 2016 in U.S. Appl. No. 13/886,867 by Cabiri.
Office Action dated May 18, 2015 in U.S. Appl. No. 13/429,942 by Cabiri.
Office Action dated May 18, 2016 in U.S. Appl. No. 13/667,739 by Cabiri.
Office Action dated May 23, 2014 in U.S. Appl. No. 13/472, 112 by Cabiri.
Office Action dated May 24, 2017 in CN Application No. 201380057196.1.
Office Action dated May 3, 2012 in CN Application No. 200880117084.X.
Office Action dated Nov. 16, 2015 in U.S. Appl. No. 13/733,516 by Cabiri.
Office Action dated Nov. 2, 2014 in CN Application No. 201180006571.0.
Office Action dated Nov. 2, 2016 in CN Application No. 201380057196.1.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2015 in U.S. Appl. No. 14/372,384 by Cabiri.

(56) References Cited

OTHER PUBLICATIONS

Office Action dated Nov. 29, 2019 in CN Application No. 201680032632.3.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 6, 2015 in U.S. Appl. No. 14/715,791 by Cabiri.
Office Action dated Oct. 11, 2017 in U.S. Appl. No. 29/605,061, by Cabiri.
Office Action dated Oct. 28, 2011 in U.S. Appl. No. 12/615,828.
Office Action dated Oct. 28, 2015 in U.S. Appl. No. 13/429,942 by Cabiri.
Office Action dated Oct. 5, 2017 in U.S. Appl. No. 29/605,068, by Cabiri.
Office Action dated Oct. 6, 2017 in U.S. Appl. No. 29/604,616, by Cabiri.
Office Action dated Oct. 6, 2017 in U.S. Appl. No. 29/605,051, by Cabiri.
Office Action dated Oct. 9, 2014 in U.S. Appl. No. 13/873,335.
Office Action dated Sep. 13, 2017 in EP Application No. 13783458.6.
Office Action dated Sep. 18, 2015 in U.S. Appl. No. 13/874,085 by Cabiri.
Office Action dated Sep. 2, 2010 in U.S. Appl. No. 12/244,688.
Office Action dated Sep. 21, 2010 in U.S. Appl. No. 12/244,666.
Office Action dated Sep. 29, 2013 in CN Application No. 201080040968.7.
Office Action dated Sep. 30, 2010 in U.S. Appl. No. 12/689,250.
Office Action dated Sep. 30, 2015 in U.S. Appl. No. 13/667,739 by Cabiri.
Office Action dated Sep. 6, 2011 in U.S. Appl. No. 12/345,818.
Office Action dated Sep. 9, 2015 in U.S. Appl. No. 13/643,470 by Alon.
Office Action dated Feb. 19, 2016 in U.S. Appl. No. 14/553,399 by Cabiri.
Office Action dated Feb. 28, 2014 in CN Application No. 201180006571.0.
Office Action dated Feb. 3, 2016 in U.S. Appl. No. 14/931,439 by Cabiri.
Office Action dated Jan. 8, 2013 in JP Application No. 2010-527595.
Office Action dated Jul. 1, 2016 in U.S. Appl. No. 15/132,740 by Cabiri.
Office Action dated Jul. 8, 2016 in CN Application No. 201510695320.8.
Office Action dated Jul. 14, 2020 in Japanese Application No. 2020-507099.
Office Action dated May 4, 2016 in U.S. Appl. No. 15/069,080 by Cabiri.

\* cited by examiner

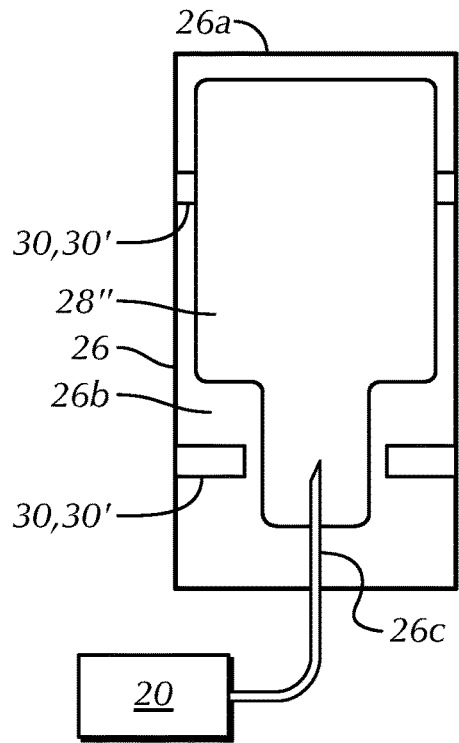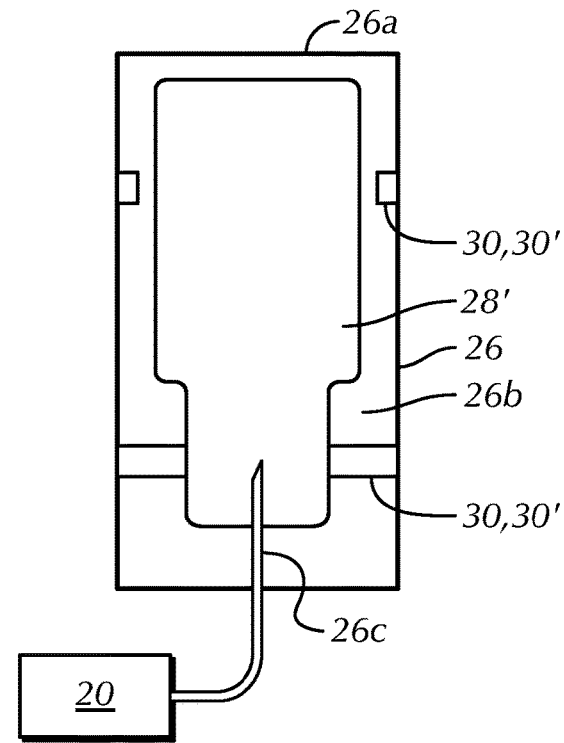
*FIG. 8A*  *FIG. 8B*
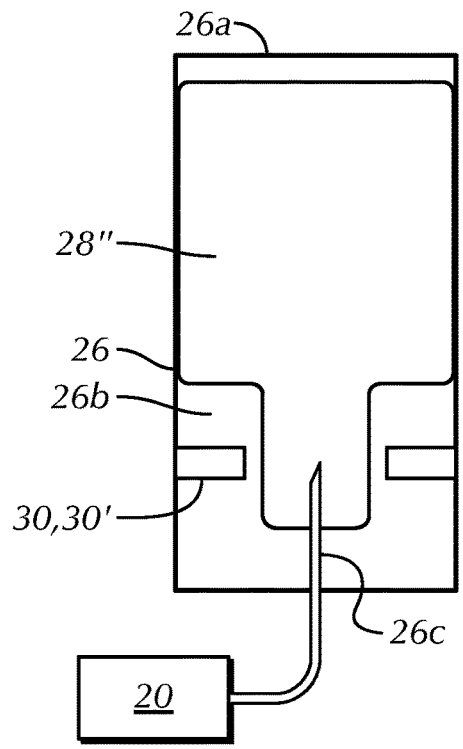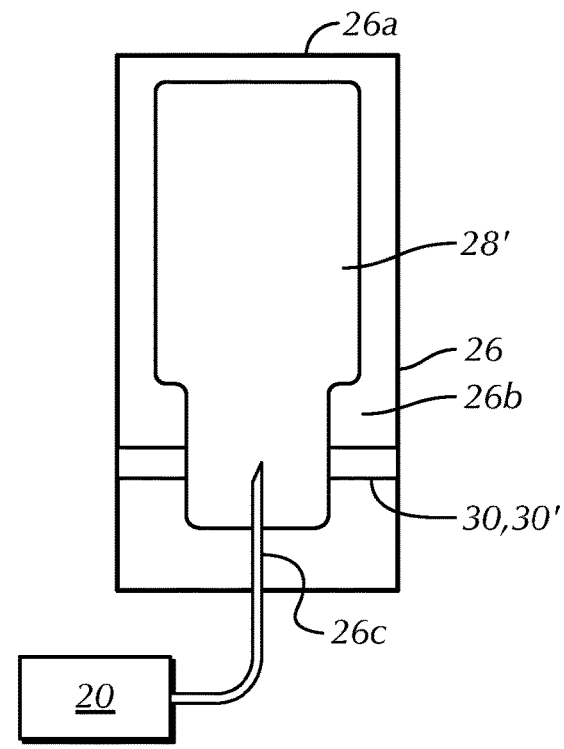
*FIG. 9A*  *FIG. 9B*

INJECTOR USABLE WITH DIFFERENT DIMENSION CARTRIDGES

CROSS-REFERENCE TO RELATED APPLICATIONS

This application is a section 371 of International Application No. PCT/US2018/066660, filed Dec. 20, 2018, which was published on Jun. 27, 2019 under International Publication No. WO 2019/126421 A1, which claims priority from U.S. Provisional Patent Application No. 62/609,740, titled "Adapter To Guide Cartridge With Integrated Shield To Protect Septum Puncture Needle From Finger Stick Hazard," filed on Dec. 22, 2017, the entire contents of which are incorporated herein by reference.

BACKGROUND OF THE DISCLOSURE

The present disclosure is generally directed to a cartridge loaded injector, and, more particularly, to an injector compatible for use with cartridges of differing dimensions.

An injector, such as, for example, a drug injector, is typically loaded with a cartridge containing therein a substance to be dispensed. The cartridge may be pre-loaded prior to delivery to a user, or, alternatively, the cartridge may be loaded by the user prior to use. Drug cartridges are manufactured and sold in different sizes and dimensions. Moreover, even cartridges manufactured via the same processes are subject to variations in dimensions, i.e., manufacturing tolerance. One or more of the manufacturing process and the material used to form the cartridges contributes to manufacturing tolerance. For example, glass cartridges are generally formed having lower precision, and, therefore, have greater variation among cartridges than cartridges formed from molded polymer(s) which are generally formed having greater precisions and lower variation among cartridges. Nevertheless, in the pharmaceutical industry, for example, glass cartridges remain more prevalent.

One drawback of conventional injectors is that they are generally manufactured to operate with a particular corresponding cartridge. Moreover, lower precision cartridges intended to work with a particular injector may nevertheless fail to be usable with the injector if formed exhibiting too large a variation from the intended dimensions.

Therefore, it would be advantageous to manufacture an injector configured to be usable with multiple differently dimensioned cartridges and cartridges subject to larger manufacturing tolerances.

BRIEF SUMMARY OF THE DISCLOSURE

Briefly stated, one aspect of the present disclosure is directed to an injector including a body, and an injection needle movably mounted to the body. The injection needle is displaceable between a retracted position and an injection position. A pathway within the body is sized for independently receiving either of a first cartridge or a radially differently dimensioned second cartridge therein. The pathway includes a proximal opening for receiving the first cartridge or the second cartridge therethrough and a coupler mounted at a distal end of the pathway and engageable with the first cartridge or the second cartridge for fluidly connecting the first cartridge or the second cartridge with the injection needle. At least two adapter collars are mounted within the pathway. A first adapter collar of the at least two adapter collars is configured to receive one of the first cartridge or the second cartridge therethrough upon insertion of the first cartridge or the second cartridge into the pathway, and configured to engage a portion of the first cartridge to stabilize the first cartridge within the pathway. A second adapter collar of the at least two adapter collars is configured to receive either of the first cartridge or the second cartridge therethrough upon insertion of the first cartridge or the second cartridge into the pathway, and configured to engage a portion of the second cartridge to stabilize the second cartridge within the pathway.

Another aspect of the present disclosure is directed to an injector including a body and an injection needle movably mounted to the body. The injection needle is displaceable between a retracted position and an injection position. A pathway within the body for receiving a cartridge includes a proximal opening for receiving the cartridge therethrough and a coupler mounted at a distal end of the pathway and engageable with the cartridge for fluidly connecting the cartridge with the injection needle. An adapter collar is mounted within the pathway and configured to receive the cartridge therethrough upon insertion of the cartridge into the pathway and is configured to engage a portion of the cartridge to stabilize the cartridge within the pathway. The adapter collar includes a disk and a plurality of angularly spaced apart cantilevered fingers projecting from the disk. The fingers are oriented in an unbiased, radially inwardly projecting closed position covering the coupler, and the fingers are deflectable distally and radially outwardly relative to one another by the cartridge into an open position exposing the coupler upon advancement of the cartridge through the disk.

Another aspect of the present disclosure is directed to an injector device kit including an injector and a plurality of adapter collars. The injector includes a body and an injection needle movably mounted to the body. The injection needle is displaceable between a retracted position and an injection position. A pathway within the body is sized for independently receiving any one of multiple radially differently dimensioned cartridges. The pathway includes a proximal opening for receiving the cartridge therethrough and a cartridge piercing needle mounted at a distal end of the pathway and projecting into the pathway, the cartridge piercing needle being in fluid communication with the injection needle and engageable with the cartridge for fluidly connecting the cartridge with the injection needle. The plurality of adapter collars are each removably mountable within the pathway, each adapter collar being configured to receive a corresponding one of the multiple radially differently dimensioned cartridges therethrough and engage a portion of the cartridge to stabilize the cartridge within the pathway and substantially co-axially align the cartridge with the cartridge piercing needle. Mounting of a respective adapter collar within the pathway enables usage of the injector with the respective corresponding cartridge.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings:

FIG. 8A is a schematic illustration of a cartridge door of the injector of FIG. 1, having a cartridge inserted therein stabilized by a proximal adapter collar of two adapter collars mounted within an interior pathway of the cartridge door;

FIG. 8B is a schematic illustration of the cartridge door of the injector of FIG. 1, having a radially differently dimensioned cartridge inserted therein stabilized by a distal adapter collar of the two adapter collars mounted within the interior pathway;

FIG. 9A is a schematic illustration of the cartridge door of the injector of FIG. 1, having a cartridge inserted therein stabilized by the interior pathway; and FIG. 9B is a schematic illustration of the cartridge door of the injector of FIG. 1, having a radially differently dimensioned cartridge inserted therein stabilized by an adapter collar mounted within the interior pathway.

DETAILED DESCRIPTION OF THE DISCLOSURE

Figure 1:
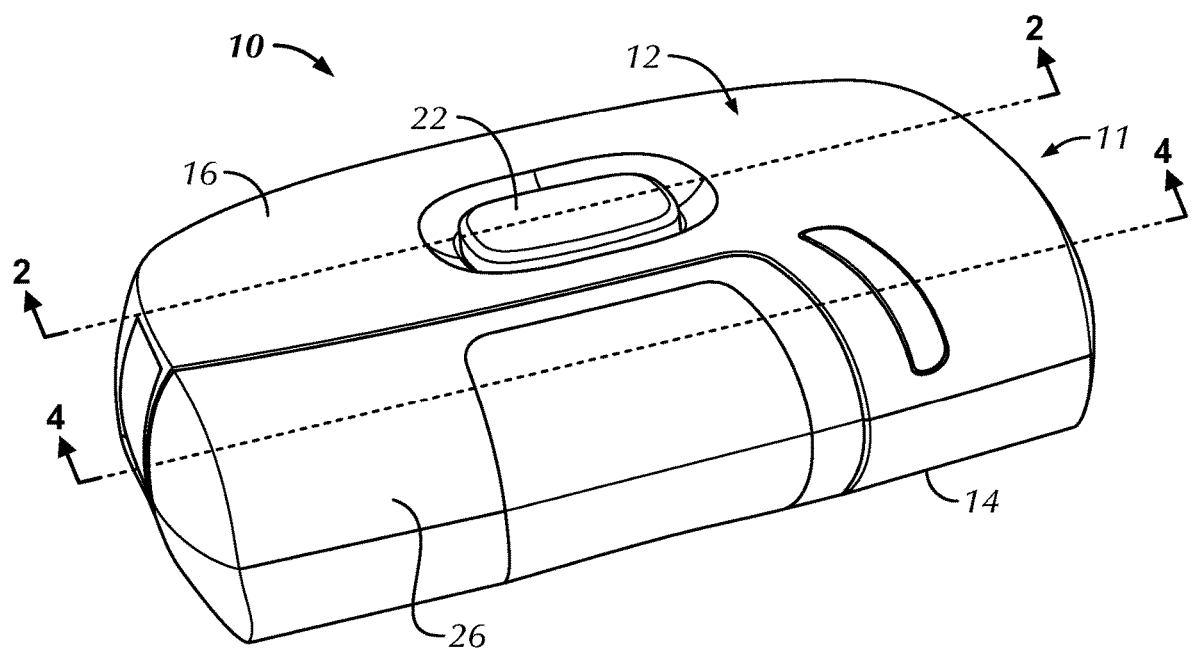
FIG. 1 is a top and front perspective view of a wearable injector, in accordance with an embodiment of the present disclosure.

Certain terminology is used in the following description for convenience only and is not limiting. For example, the words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-9B an injector, generally designated 10, in accordance with an embodiment of the present disclosure. In the illustrated embodiment, the injector 10 takes the form of a wearable injector (patch injector), such as, for example, without limitation, a wearable drug injector, but the disclosure is not so limited. As should be understood by those of ordinary skill in the art, the injector 10 generally includes a body 11. The body 11 includes a main housing 12 having a first surface 14 configured to contact a skin surface of a user (not shown), e.g., a patient, the first surface 14 having an opening 14a therein. In the illustrated embodiment, the first surface 14 defines a base surface of the injector main housing 12, but the disclosure is not so limited. The main housing 12 also includes a second surface 16 opposing the first surface 14. In the illustrated embodiment, the second surface 16 defines a top, external surface of the injector main housing 12, but the disclosure is not so limited.

Figure 2:
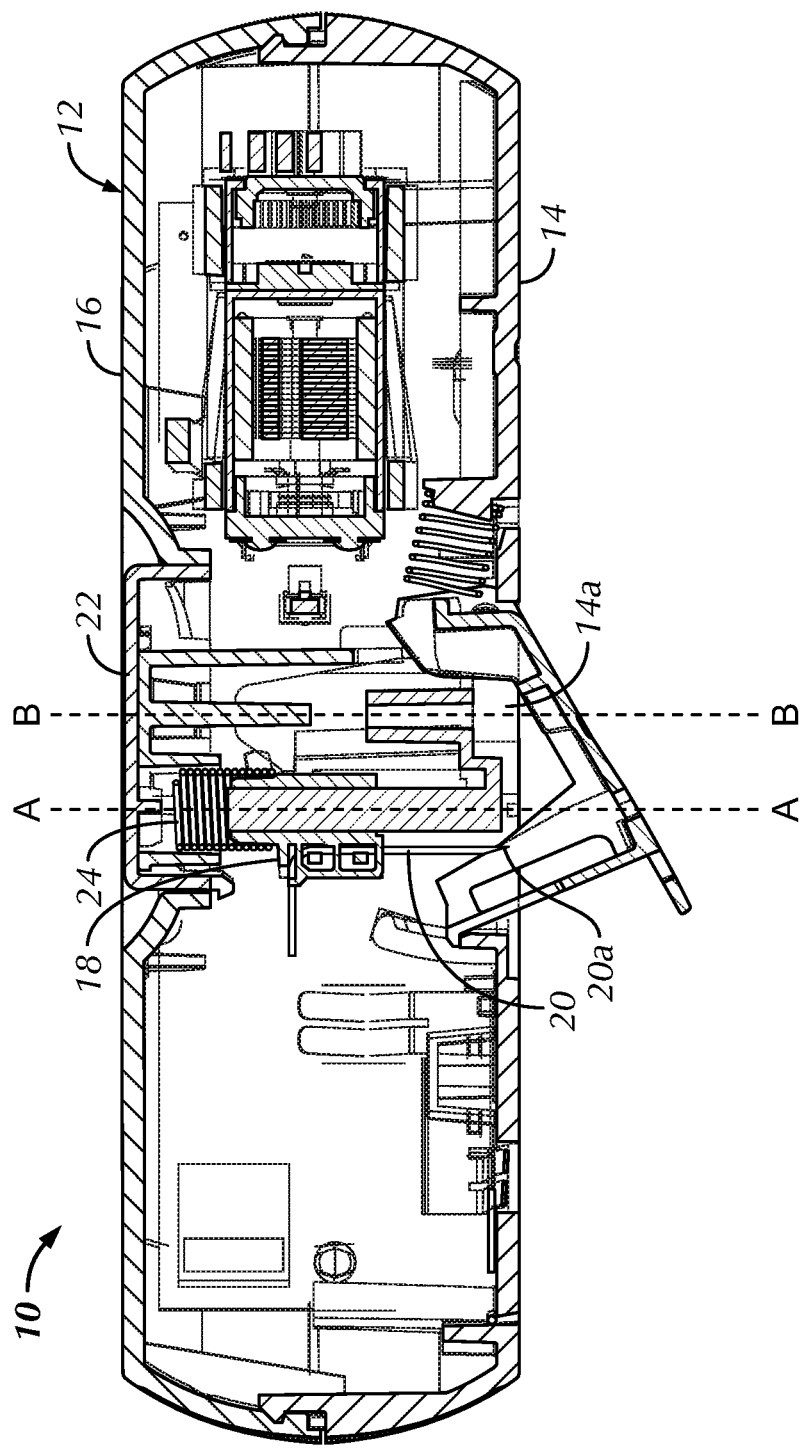
FIG. 2 is a cross-sectional view of the injector of FIG. 1, taken along the sectional line 2-2 of FIG. 1, with an activation button assembly in an unactuated position thereof and an injection needle in a retracted position thereof.
Figure 3:
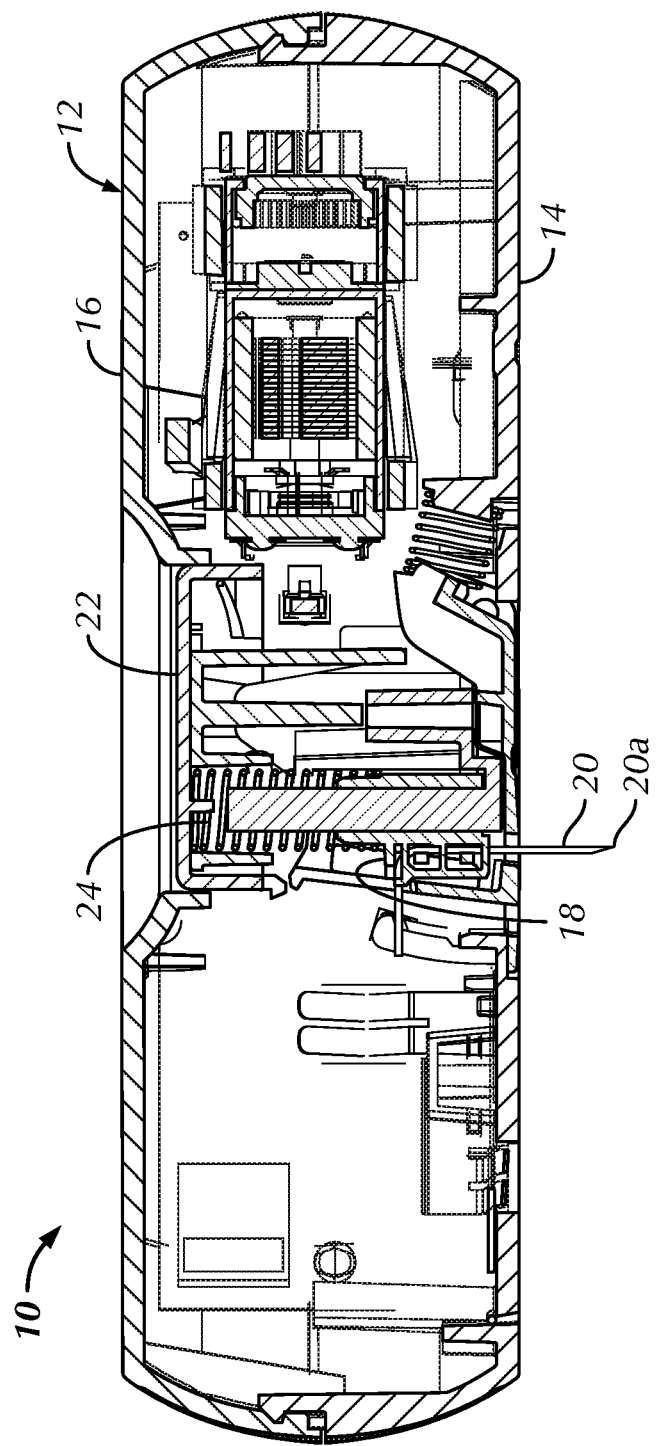
FIG. 3 is a cross-sectional view of the injector of FIG. 1, taken along the sectional line 2-2 of FIG. 1, with the activation button assembly in an actuated position thereof and the injection needle in an injection position thereof.

As shown in FIGS. 2-3, a needle hub 18, constructed, for example, from a polymeric or metal material, combinations thereof, or the like, is movably mounted within the main housing 12 of the injector body 11 and an injection needle 20 is supported by the movable needle hub 18 in a manner well understood by those of ordinary skill in the art. In the illustrated embodiment, the needle hub 18 and the injection needle 20 are axially translatable (or otherwise displaceable) in the direction of axis A (FIG. 2) extending substantially perpendicularly to the first surface 14, between a retracted position (FIG. 2), wherein at least a tip 20a of the injection needle 20 is contained within the injector main housing 12, and an injection position (FIG. 3), wherein at least the tip 20a of the injection needle 20 protrudes from the injector main housing 12 through the opening 14a. As should be understood by those of ordinary skill in the art, however, the axis A may be positioned at angles other than 90° relative to the first surface 14. As also should be understood, the injection needle 20 may be movably mounted within the injector main housing 12 via mechanisms other than the needle hub 18.

In some embodiments, a depressible activation button assembly 22, constructed, for example, from a polymeric or metal material, combinations thereof, or the like, may be movably mounted to the injector main housing 12 and operatively connected to the injection needle 20. The activation button assembly 22 may be translatable, i.e., depressible, along a button axis B (FIG. 2) from an unactuated position (FIGS. 1, 2) to an actuated position (FIG. 3) in a manner well understood by those of ordinary skill in the art, to activate the injector 10. In one embodiment, the button axis B may be parallel to the axis A, but the disclosure is not so limited. Activation of the injector 10 includes, for example, driving the injection needle 20 from the retraction position to the injection position thereof to perform an injection.

A biasing member 24 may be operatively connected with the activation button assembly 22 and the injection needle 20 (FIGS. 2, 3), but the disclosure is not so limited. As one alternative example, the biasing member 24 may be connected with the second surface 16 and the injection needle 20. The biasing member 24 is stabilized in a stored energy state in the unactuated position of the activation button assembly 22 (FIG. 2) and released into an energy releasing state, when the activation button assembly 22 is translated into the actuated position thereof (FIG. 3), to drive the injection needle 20 along the direction of axis A from the retracted position thereof to the injection position thereof. As should be understood by those of ordinary skill in the art, the stored energy state of the biasing member 24 is a state in which the biasing member 24 stores at least some potential energy. The energy releasing state of the biasing member 24 is a state of the biasing member 24 in which the biasing member 24 releases at least some of the previously stored potential energy from the stored energy state.

In one embodiment, the biasing member 24 may take the form of a coil spring mounted between the needle hub 18 and the activation button assembly 22, i.e., the spring 24 abuts the activation button assembly 22 at one end and abuts the needle hub 18 at an opposing end. In the energy storing state, the coil spring 24 is at least partially compressed. In the energy releasing state, the coil spring 24 expands (relative to the at least partially compressed energy storing state) to drive the needle hub 18 and the injection needle 20 into the injection position thereof. As should be understood by those of ordinary skill in the art, however, the biasing member 24 may alternatively take the form of other members capable of storing and releasing energy. Non-limiting examples include other springs (e.g., torsion or leaf springs), elastic bands, and the like. Alternatively, the biasing member 24 may take the form of an electromechanical or pneumatic actuator configured to apply a translational force onto the injection needle 20 when the activation button assembly 22 is depressed into the actuated position thereof.

Figure 4A:
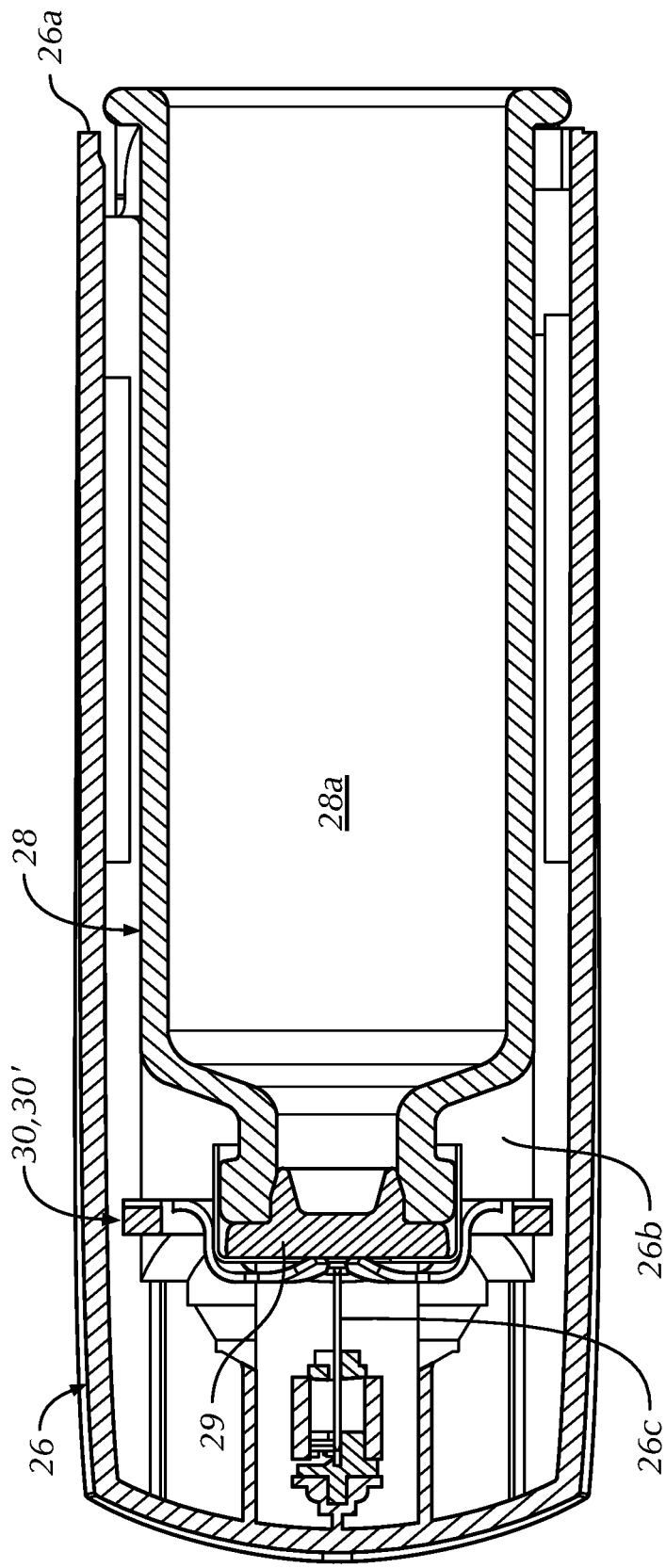
FIG. 4A is a partial cross-sectional view of the injector of FIG. 1, taken along the sectional line 4-4 of FIG. 1, the injector having an adapter collar mounted therein with cantilevered fingers thereof in a closed position.

The injector body 11 further includes a cartridge door 26 movably, e.g., pivotably, mounted to the injector main housing 12, between an open position (not shown) and a closed position (FIG. 1). As shown in FIG. 4A, the cartridge door 26 includes a proximal open end 26a and an interior pathway 26b for receiving (in the open position of the door) one of a plurality of differently dimensioned cartridges 28 therein, e.g., at least a first cartridge 28' or a differently dimensioned second cartridge 28" e.g., radially different, (as will be described in further detail below, see, e.g., FIGS. 8A-9B). As should be understood, a cartridge 28 usable with the injector 10 includes a reservoir 28a containing a substance (not shown), e.g., medicament, to be dispensed from the injector 10 through the injection needle 20, and having a first, distal opening sealed by a pierceable septum 29 in a manner well understood by those of ordinary skill in the art.

The cartridge door 26 further includes a coupler 26c mounted within the interior pathway 26b. In the illustrated embodiment, the coupler 26c takes the form of a cartridge piercing needle 26c, but the disclosure is not so limited. As shown schematically in FIGS. 8A-9B, the cartridge piercing needle 26c is fluidly connected to the injection needle 20 in a manner well understood by those of ordinary skill in the art, e.g., via a flexible tube (partially shown in FIGS. 4B, 5) extending from the piercing needle 26c to the injection needle 20. In the illustrated embodiment, the cartridge piercing needle 26c is positioned proximate a closed, distal end of the interior pathway 26b, opposite the proximal open end 26a (FIGS. 4A, 8A-9B). The cartridge piercing needle 26c extends inwardly into the interior pathway 26b and terminates at a tip of the needle 26c, positioned to face and align with the pierceable septum 29 of the cartridge 28 when the cartridge 28 is inserted into the cartridge door 26. The cartridge piercing needle 26c is configured to fully penetrate the pierceable septum 29 of the cartridge 28 to fluidly connect the substance within the cartridge 28 with the injection needle 20 when the cartridge 28 is sufficiently inserted into the interior pathway 26b and/or when the injector 10 is activated.

Figure 4B:
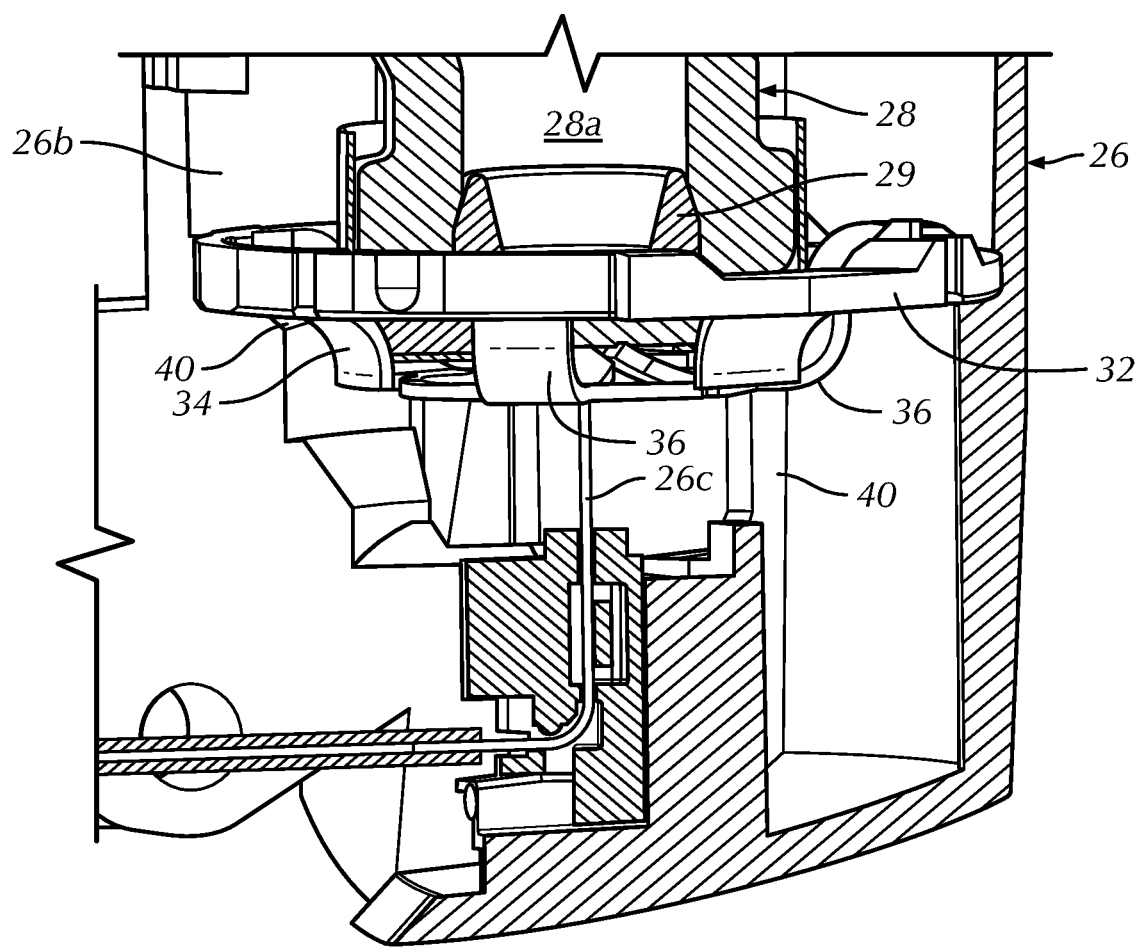
FIG. 4B is an enlarged, partial view of FIG. 4A.
Figure 5:
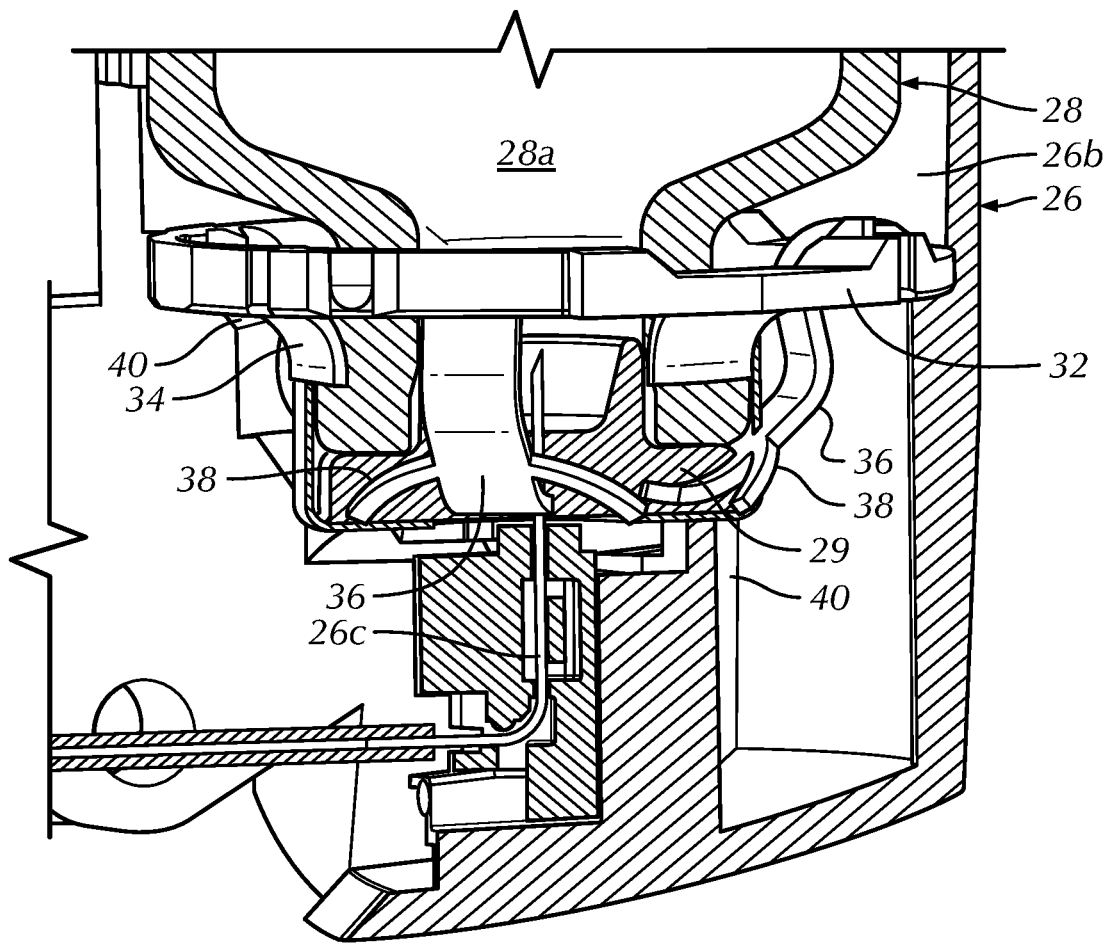
FIG. 5 is an enlarged, partial view of FIG. 4A with the cantilevered fingers of the adapter collar in an open position and the cartridge pierced by a cartridge piercing needle of the injector.

As shown in FIGS. 4-5, at least one adapter collar 30, 30' is mountable within the interior pathway 26b (in an orientation generally transverse to the cartridge insertion path). The adapter collar 30, 30' is configured, i.e., sized and dimensioned, to receive any cartridge 28 usable with the injector 10 therethrough upon insertion of the cartridge 28 into the interior pathway 26b, and configured to engage a portion of a particularly dimensioned corresponding cartridge 28 to stabilize the cartridge 28 within the interior pathway 26b.

Figure 6A:
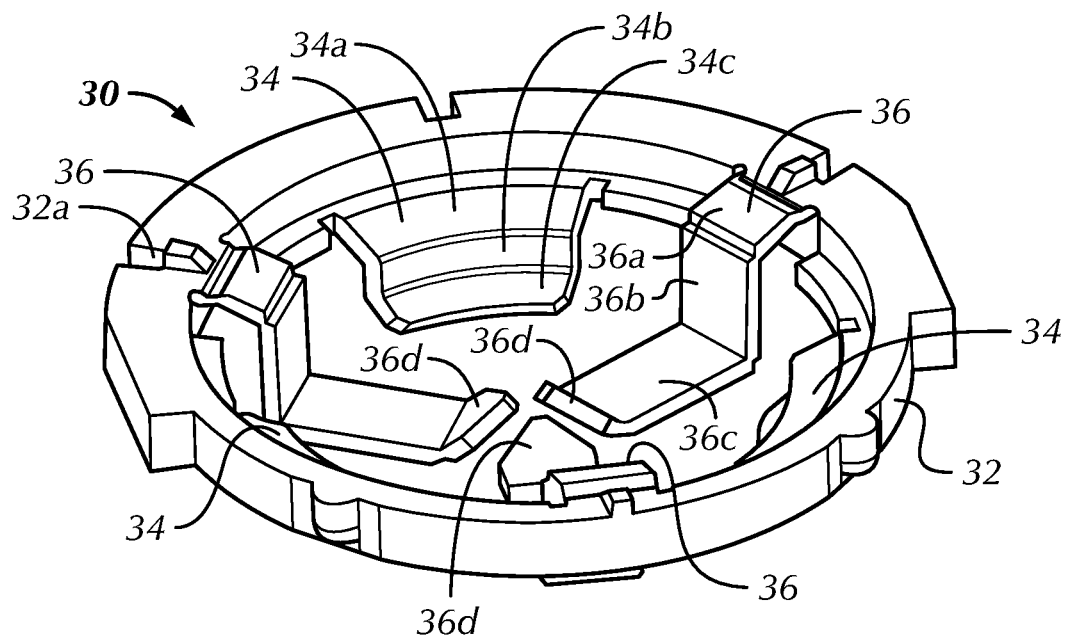
FIG. 6A is a perspective view of a first configuration of an adapter collar of the invention with the cantilevered fingers thereof in the closed position.
Figure 6B:
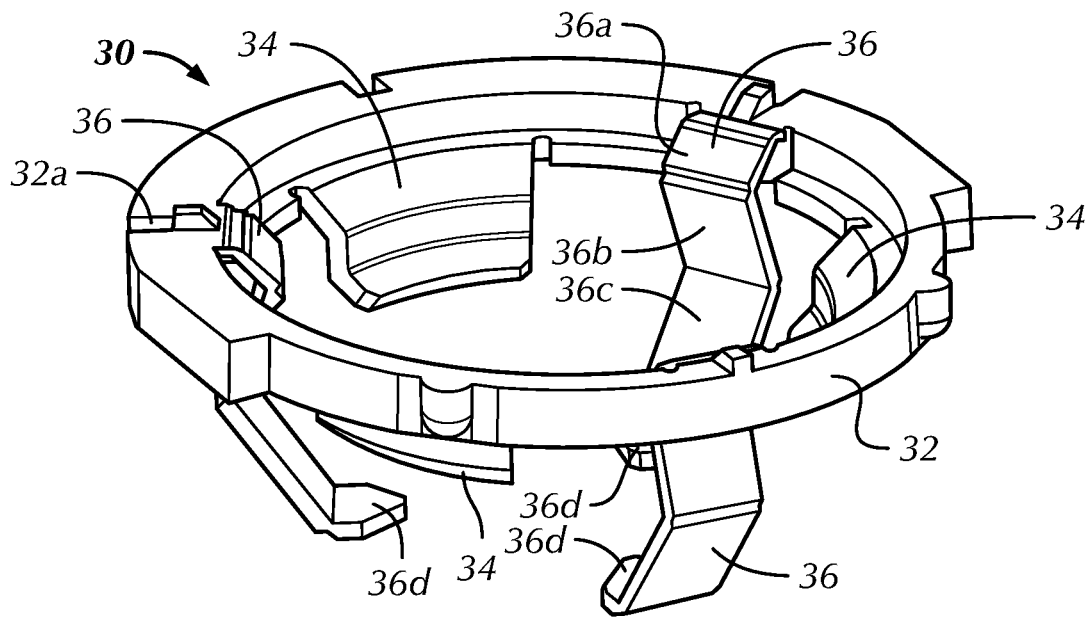
FIG. 6B is a perspective view of the adapter collar of FIG. 6A, with the cantilevered fingers thereof in the open position.

In one configuration, as shown best in FIGS. 6A-6B, the adapter collar 30 includes a disk 32 and a plurality of angularly spaced ribs 34 projecting radially inwardly into the interior pathway 26b from the disk 32. In the illustrated embodiment, the adapter collar 30 includes three ribs 34 generally equally angularly spaced apart about the interior of the disk 32, but the disclosure is not so limited. The ribs 34 are substantially equally sized, dimensioned and configured to engage and stabilize the corresponding cartridge 28 in a position aligned, e.g., substantially co-axially, with the cartridge piercing needle 26c.

In one configuration, as shown in FIGS. 6A-6B, one or more of the ribs 34 each includes a first segment 34a projecting primarily radially inwardly from the disk 32, a second segment 34b projecting primarily distally (i.e., toward the cartridge piercing needle 26c) from the first segment 34a and a third segment 34c projecting primarily radially inwardly from the second segment 34b. The first and third segments 34a and 34c may also be slightly angled distally and/or be distally flexible upon engagement of the ribs 34 with a cartridge 28 to better align the cartridge 28 with the cartridge piercing needle 26c. As should be understood by those of ordinary skill in the art, however, the ribs 34 may be employed in alternative configurations capable of performing the function of the ribs 34 described herein.

In some embodiments, the adapter collar 30 may also include a plurality of angularly spaced apart cantilevered fingers 36 projecting from the disk 32. In the illustrated embodiment, the adapter collar 30 includes three fingers 36 generally equally angularly spaced apart about the interior of the disk 32, but the disclosure is not so limited. As shown in FIGS. 4A, 4B and 6A, the fingers 36 are oriented in a radially inwardly projecting, closed position when unbiased by a cartridge 28, i.e., when a cartridge 28 has not been advanced past the fingers 36. The fingers 36 are dimensioned, such that the fingers 36 cover the cartridge piercing needle 26c when in the closed position. For example, the fingers 36 may extend radially inwardly proximate to the central axis of the disk 32. Thus, in the closed position thereof, the fingers 36 assist in preventing contact between the cartridge piercing needle 26c and a user's hands/fingers (or other of a user's body parts), and, therefore, assist in preventing needle stick injuries.

As shown in FIGS. 5 and 6B, the cantilevered fingers 36 are deflectable distally and radially outwardly (generally at the interface between the finger 36 and the disk 32) relative to one another into an open position exposing the cartridge piercing needle 26c, upon advancement of a cartridge 28 beyond the disk 32. That is, the cartridge 28 deflects the fingers 36 into the open position thereof upon advancement of the cartridge 28 beyond the position of the fingers 36 in the closed position thereof, exposing the cartridge piercing needle 26c to penetrate the septum 29 of the cartridge 28.

In one configuration, as shown in FIGS. 6A-6B, one or more of the fingers 36 each include a first segment 36a projecting primarily radially inwardly from the disk 32. The interface between the first segment 36a and the disk 32 may define, for example, a living hinge having a natural bias to orient in the closed position in the absence of an external force by a cartridge 28. A second segment 36b projects primarily distally from the first segment 36a and a third segment 36c projects primarily radially inwardly from the second segment 36b. A fourth segment 36d may project further radially inwardly and also project proximally from the third segment 36c to provide additional vertical clearance above the cartridge piercing needle 26c. One or more of the segments 36a-36d may also define living hinges at the respective interfaces therebetween to provide additional flexibility to the fingers 36. As should be understood, the lengths of the segments 36a-d behave as moment arms for the deflection of the fingers 36. Accordingly, the lengths of the segments 36a-d may be configured to generally set the advancement force required by a cartridge 28 to deflect the fingers 36 from the closed position to the open position thereof. As also should be understood by those of ordinary skill in the art, the fingers 36 may be employed in alternative configurations capable of performing the function of the fingers 36 described herein.

Figure 7A:
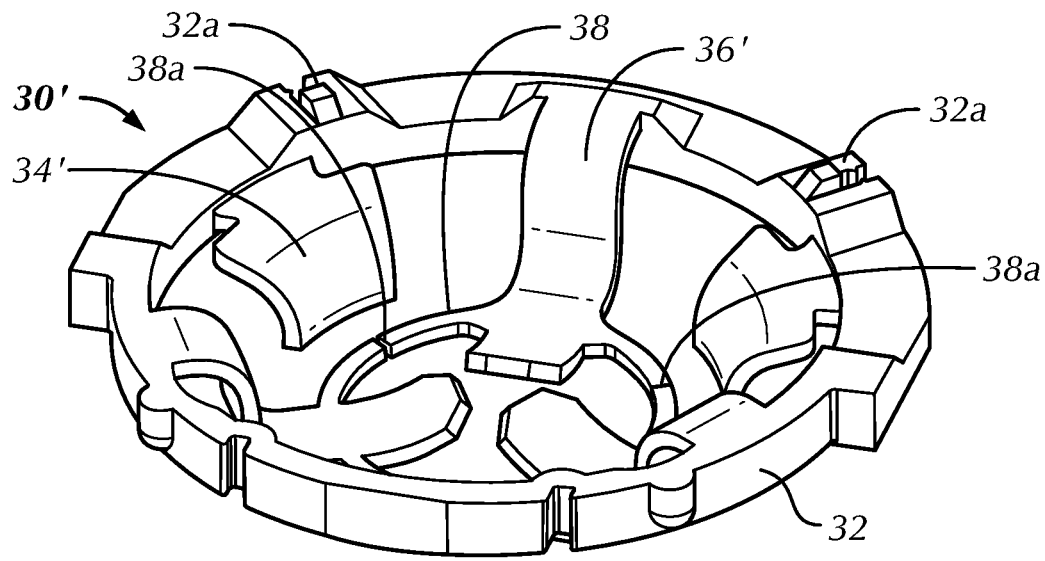
FIG. 7A is a perspective view of a second configuration of an adapter collar of the invention with the cantilevered fingers thereof in the closed position and an intact frangible ring connecting the cantilevered fingers.
Figure 7B:
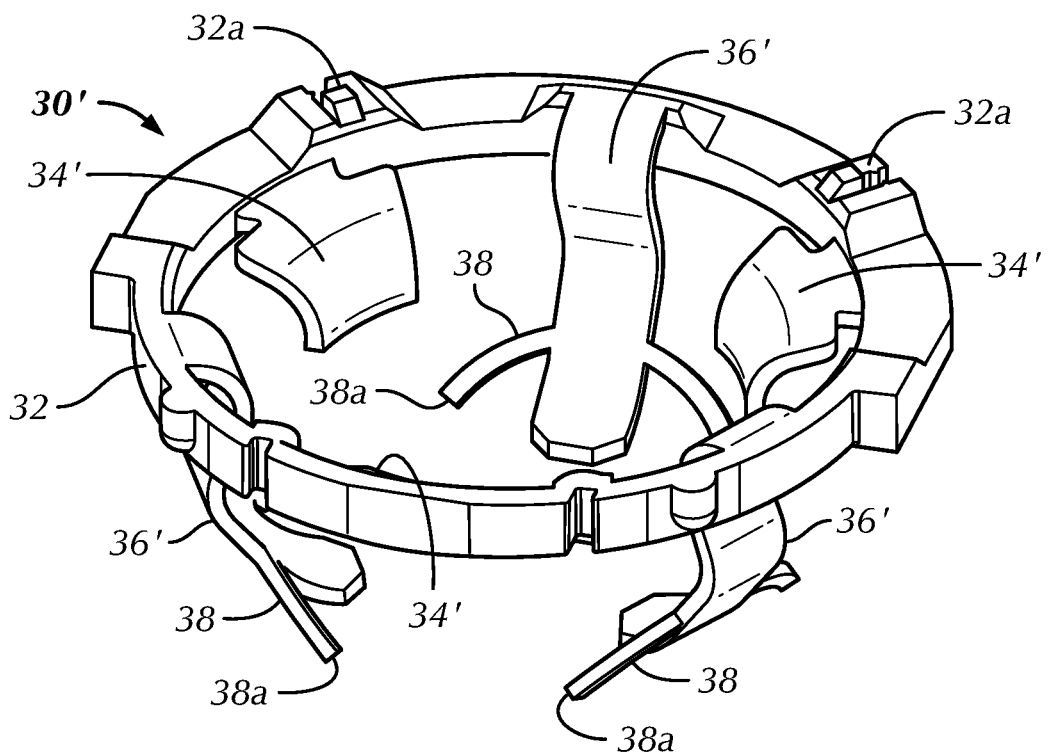
FIG. 7B is a perspective view of the adapter collar of FIG. 7A, with the cantilevered fingers thereof in the open position, fracturing the frangible ring.

FIGS. 7A-7B illustrate an alternative configuration of the adapter collar 30'. This configuration is similar to that of the configuration of FIGS. 6A-6B, and, therefore, the description of certain similarities between the configurations of FIGS. 7A-7B and FIGS. 6A-6B may be omitted herein for the sake of brevity and convenience, and, therefore, is not limiting.

One difference of the adapter collar 30' over the adapter collar 30 (as shown in the figures) is the addition of a frangible, i.e., intentionally breakable, member 38 connecting the cantilevered fingers 36' to one another in the closed position thereof. In the illustrated embodiment, the frangible member 38 takes the form of a frangible ring, but the disclosure is not so limited. As shown best in FIG. 7A, the frangible ring 38 includes at least one scored segment 38a, e.g., a scored segment 38a between each cantilevered finger 36', defining the intentionally breakable segment(s) of the ring 38 (FIG. 7B). As should be understood by those of ordinary skill in the art, the scored segments 38a of the frangible ring 38 define a pre-set breaking force of the frangible ring 38, which must be exceeded to separate and disconnect the ring 38 in order to separate and disconnect the fingers 36' from one another and deflect the fingers 36' from the closed position to the open position thereof. As should be understood, the fingers 36 of the adapter collar 30 may also be joined by frangible members similar to the frangible member 38 joining the fingers 36' of the adapter collar 30'.

In one configuration of the adapter collar 30', one or more of ribs 34' takes the form of a generally arcuate member extending radially inwardly and distally from the disk 32, having a convex surface thereof facing toward the central axis of the disk 32, but the disclosure is not so limited. Additionally, or alternatively, one or more of the cantilevered fingers 36' defines a generally S-shaped curvilinear contour, extending radially inwardly and distally from the disk 32 (assisting in cartridge 28 lead in), but the disclosure is not so limited.

As shown best in FIGS. 4A-5, at least one adapter collar 30, 30' is mounted within the interior pathway 26b. In one configuration, the adapter collar 30, 30' may be removably mounted within the interior pathway 26b (intentionally removable without damaging the collar 30, 30' and/or the interior pathway 26b). For example, the interior pathway 26b may include a radially inwardly extending annular lip 40 projecting from the sidewall of the interior pathway 26b, or radially inwardly extending lip segments 40 projecting from the sidewall of the interior pathway 26b angularly spaced (in substantially the same plane) about the sidewall, upon which the adapter collar 30, 30' may be supported. Alternatively, or additionally, the adapter collar 30, 30' may be mounted within the interior pathway 26b via a friction fit with the sidewall of the interior pathway 26b. In one embodiment, the adapter collar 30, 30' may include mounting slot 32a in the disk 32 thereof, for receiving the annular lip segments 40. As should be understood by one those of ordinary skill in the art, however, the adapter collar 30, 30' may be removably mounted within the interior pathway 26b via any of numerous mounting means currently known, or that later become known. Alternatively, an adapter collar 30, 30' may be permanently (i.e., non-removable without damaging the collar 30, 30' and/or the interior pathway 26b) mounted within the interior pathway 26b or integrally formed with the interior pathway 26b. For injectors 10 having more than one adapter collar 30, 30' mounted within the interior pathway 26b thereof (as will be discussed in further detail below), the adapter collars 30, 30', may be integrally, permanently or removably mounted therein, or any combination thereof.

In use, an injector 10 includes at least one adapter collar 30, 30' mounted within the interior pathway 26b, corresponding to a cartridge 28 intended for use with the injector 10 (FIGS. 4A, 4B). The cartridge 28 is inserted into the interior pathway 26b via the proximal open end 26a thereof and advanced through the adapter collar 30, 30' and into engagement with the cartridge piercing needle 26c (FIG. 5), i.e., piercing the septum 29. The adapter collar 30, 30' is configured (via the size and dimension of the ribs 34, 34') to engage a portion of the corresponding cartridge 28 to stabilize the cartridge 28 within the interior pathway 26b and align, e.g., substantially co-axially, the cartridge 28 with the cartridge piercing needle 26c. In configurations where the adapter collar 30, 30' includes the cantilevered fingers 36, 36', the fingers 36, 36' protect the user against inadvertent needle stick injuries from the cartridge piercing needle 26c in the closed position. During insertion of the cartridge 28 into the interior pathway 26b, the cartridge 28 engages and deflects the fingers 36, 36' into the open position thereof upon advancement beyond the fingers 36, 36' and into engagement with the cartridge piercing needle 26c (FIG. 5).

In some embodiments, the injector 10 may be configured to be usable with cartridges 28 of different sizes. For example, as shown schematically, in FIGS. 8A-9B, the injector 10 may be configured for use with at least two differently dimensioned cartridges: a first cartridge 28' and a second cartridge 28". Accordingly, the interior pathway 26b is sized, e.g., in diameter, to receive either of the first cartridge 28' or second cartridge 28".

In one exemplary non-limiting embodiment, the interior pathway 26c may include at least two of the adapter collars 30, 30' mounted therein (two of the adapter collars 30, 30' shown in FIGS. 8A, 8B). As shown in the non-limiting example of FIGS. 8A and 8B, the first cartridge 28' may define a radially larger distal portion relative to the distal portion of the second cartridge 28", and the second cartridge 28" may define a radially larger proximal portion relative to the proximal portion of the first cartridge 28'. A first adapter collar 30, 30', therefore, is mounted distally within the interior pathway 26c relative to the second adapter collar 30, 30'.

The first, distal adapter collar 30, 30' is sized and positioned within the interior pathway 26b to permit advancement of either one of the first cartridge 28' or the second cartridge 28" therethrough upon insertion of that cartridge into the interior pathway 26b. As shown in FIG. 8B, the first, distal adapter collar 30, 30' is sized and positioned, however, to only engage a distal portion of the first cartridge 28' to stabilize the first cartridge 28' within the interior pathway 26b, and align the first cartridge 28' with the cartridge piercing needle 26c. That is, the ribs 34, 34' of the first, distal adapter collar 30, 30' are sized and dimensioned to engage the distal portion of the first cartridge 28', without interfering with the smaller distal portion of the second cartridge 28" if the second cartridge 28" was to be utilized with the injector 10.

Similarly, the second, proximal adapter collar 30, 30' is also sized and positioned within the interior pathway 26b to permit advancement of either one of the first cartridge 28' or the second cartridge 28" therethrough upon insertion of that cartridge into the interior pathway 26b. Conversely, however, as shown in FIG. 8A, the second, proximal adapter collar 30, 30' is sized and positioned to only engage a proximal portion of the second cartridge 28" to stabilize the second cartridge 28" within the interior pathway 26b, and to align the second cartridge 28" with the cartridge piercing needle 26c. That is, the ribs 34, 34' of the second, proximal adapter collar 30, 30' are sized and dimensioned to engage the proximal portion of the second cartridge 28", without interfering with the first cartridge 28' if the first cartridge 28' was to be utilized with the injector 10. Therefore, in the embodiment of FIGS. 8A, 8B, the second cartridge 28" is not obstructed by either of the adapter collars 30, 30' mounted within the interior pathway 26b, and the first cartridge 28' is also not obstructed by either of the adapter collars 30, 30' mounted within the interior pathway 26b. Either of the two cartridges 28', 28" is usable with the injector 10, however, as either cartridge 28', 28" may be stabilized within the interior pathway 26b and aligned with the cartridge piercing needle 26c.

In some embodiments, some of the adapter collars 30, 30' mounted within the interior pathway 26b, such as, for example, the distal-most adapter collar, may include the plurality of angularly spaced apart cantilevered fingers 36, 36' projecting from the disk 32 to assist in preventing contact between a user's hands/fingers (or other of a user's body parts) and the cartridge piercing needle 26c, and, therefore, assist in preventing needle stick injuries. Alternatively, all or none of the adapter collars 30, 30' mounted within the interior pathway 26b may include the cantilevered fingers 36, 36'.

In an alternative exemplary non-limiting embodiment, as shown in FIGS. 9A, and 9B, the interior pathway may include solely the distal adapter collar 30, 30' as shown in FIGS. 8A and 8B, configured in like manner as the distal adapter collar 30, 30' described with respect to FIGS. 8A and 8B to stabilize the first cartridge 28' within the interior pathway 26b, and to align the first cartridge 28' with the cartridge piercing needle 26c (FIG. 9B). Conversely, the interior pathway 26b itself, i.e., the internal features thereof, may be configured to stabilize the second cartridge 28" within the interior pathway 26b, and to align the second cartridge 28" with the cartridge piercing needle 26c (FIG. 9A). For example, without limitation, the interior pathway 26b may be dimensioned or include a cartridge cradle, a cartridge track, combinations thereof, or the like (not shown) to receive and stabilize the cartridge 28 in the interior pathway 26b.

In one configuration, the injector 10 may be provided as a kit with a plurality of adapter collars 30, 30' removably mountable within the interior pathway 26b. The interior pathway 26b may be configured to receive any one of multiple different dimensioned cartridges 28, i.e., sized and dimensioned to receive the largest of those cartridges 28. Each adapter collar 30, 30' provided may be configured, i.e., sized and dimensioned, for use with a corresponding one of the multiple differently dimensioned cartridges 28, to engage a portion of the corresponding cartridge 28 (with the ribs 34, 34' thereof) to stabilize the cartridge 28 within the interior pathway 26b and align the cartridge 28 with the cartridge piercing needle 26c. Alternatively, or additionally, adapter collars 30, 30' provided may be configured to account for variations between cartridges 28 due to manufacturing tolerances. Accordingly, a user may mount a particular adapter collar 30, 30' within the interior pathway 26b to enable usage of the injector 10 with the respective corresponding cartridge 28 prior to inserting the corresponding cartridge 28 into the interior pathway 26b.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as set forth in the appended claims.

We claim:

1. An injector comprising:
   a body;
   an injection needle movably mounted to the body, the injection needle being displaceable between a retracted position and an injection position;
   a pathway within the body sized for independently receiving either of a first cartridge or a second cartridge therein, wherein a radial dimension of the first cartridge is different than a radial dimension of the second cartridge, the pathway including a proximal opening for receiving the first cartridge or the second cartridge therethrough and a coupler mounted at a distal end of the pathway and engageable with the first cartridge or the second cartridge for fluidly connecting the first cartridge or the second cartridge with the injection needle;
   a first adapter collar mounted within the pathway; and
   a second adapter collar mounted within the pathway,
   wherein the first adapter collar is configured to receive one of the first cartridge or the second cartridge therethrough upon insertion of the first cartridge or the second cartridge into the pathway, and the first adapter collar is configured to engage a portion of the first cartridge to stabilize the first cartridge within the pathway,
   wherein the second adapter collar is configured to receive either of the first cartridge or the second cartridge therethrough upon an insertion of the first cartridge or the second cartridge into the pathway, and the second adapter collar is configured to engage with the second cartridge to stabilize the second cartridge within the pathway,
   wherein each of the first adapter collar and the second adapter collar comprises a disk,
   wherein the first adapter collar comprises fingers that are cantilevered, angularly spaced apart from each other, and that project from the disk of the first adapter collar the fingers being oriented in an unbiased, radially inwardly projecting closed position covering the coupler, and the fingers being deflectable distally and radially outwardly relative to one another by the first into an open position exposing the coupler upon advancement of the first through the disk of the first adapter collar, and wherein in the unbiased, radially inwardly projecting closed position the fingers extend radially inwardly to positions that are radially between a central axis of the disk of the first adapter collar and an inner wall of a neck of the first cartridge.

2. The injector of claim 1, wherein the first adapter collar is configured to substantially co-axially align the first cartridge with the coupler, and wherein the second adapter collar is configured to substantially co-axially align the second cartridge with the coupler.

3. The injector of claim 1, wherein at least one of the first adapter collar or the second adapter collar is removably mounted within the pathway.

4. The injector of claim 1, wherein the first cartridge defines a radially larger distal portion relative to the second cartridge and wherein the second cartridge defines a radially larger proximal portion relative to the first cartridge, and wherein the first adapter collar is distally located within the pathway relative to the second adapter collar.

5. The injector of claim 1, wherein each of the first adapter collar and the second adapter collar comprises ribs that are angularly spaced apart from each other and that project radially inwardly into the pathway from the respective disk, the ribs of the first adapter collar being configured to engage the portion of the first cartridge and the ribs of the second adapter collar being configured to engage the portion of the second cartridge.

6. The injector of claim 1, wherein the coupler comprises a cartridge piercing needle projecting into the pathway, the cartridge piercing needle being in fluid communication with the injection needle.

7. The injector of claim 1, wherein the fingers are connected to one another in the unbiased, radially inwardly projecting closed position by a frangible member, the frangible member defining a pre-set breaking force which must be exceeded to separate and disconnect the fingers from one another and deflect the fingers from the unbiased, radially inwardly projecting closed position to the open position.

8. The injector of claim 7, wherein the frangible member comprises a frangible ring.

9. An injector comprising:
a body;
an injection needle movably mounted to the body, the injection needle being displaceable between a retracted position and an injection position;
a pathway within the body for receiving a cartridge, the pathway including a proximal opening for receiving the cartridge therethrough and a coupler mounted at a distal end of the pathway and engageable with the cartridge for fluidly connecting the cartridge with the injection needle; and
an adapter collar mounted within the pathway and configured to receive the cartridge therethrough upon insertion of the cartridge into the pathway and configured to engage a portion of the cartridge to stabilize the cartridge within the pathway, the adapter collar comprising a disk and fingers that are cantilevered, angularly spaced apart from each other, and that project from the disk, the fingers being oriented in an unbiased, radially inwardly projecting closed position covering the coupler, and the fingers being deflectable distally and radially outwardly relative to one another by the cartridge into an open position exposing the coupler upon advancement of the cartridge through the disk.

10. The injector of claim 9, wherein the adapter collar is configured to substantially co-axially align the cartridge with the coupler.

11. The injector of claim 9, wherein the coupler comprises a cartridge piercing needle projecting into the pathway, the cartridge piercing needle being in fluid communication with the injection needle.

12. The injector of claim 9, wherein the fingers are connected to one another in the unbiased, radially inwardly projecting closed position by a frangible member, the frangible member defining a pre-set breaking force which must be exceeded to separate and disconnect the fingers from one another and deflect the fingers from the unbiased, radially inwardly projecting closed position to the open position.

13. The injector of claim 12, wherein the frangible member comprises a frangible ring.

14. The injector of claim 9, wherein the adapter collar is removably mounted within the pathway.

15. The injector of claim 9, wherein the adapter collar further comprises ribs that are angularly spaced apart from each other and that project radially inwardly into the pathway from the disk, the ribs being configured to engage the portion of the cartridge.

16. The injector of claim 9, wherein when the cartridge is advanced through the disk the fingers are configured to deflect continuously radially outwardly between the unbiased, radially inwardly projecting closed position and the open position.

17. An injector device kit comprising:
an injector having:
a body;
an injection needle movably mounted to the body, the injection needle being displaceable between a retracted position and an injection position;
a pathway within the body sized for independently receiving any one of a plurality of radially differently dimensioned cartridges, the pathway including a proximal opening for receiving the plurality of radially differently dimensioned cartridges therethrough and a cartridge piercing needle mounted at a distal end of the pathway and projecting into the pathway, the cartridge piercing needle being in fluid communication with the injection needle and engageable with the plurality of radially differently dimensioned cartridges for fluidly connecting the plurality of radially differently dimensioned cartridges with the injection needle; and
a plurality of adapter collars each removably mountable within the pathway, each adapter collar being configured to receive a corresponding one of the plurality of radially differently dimensioned cartridges therethrough and engage a portion of the corresponding one of the plurality of radially differently dimensioned cartridges to stabilize the corresponding one of the plurality of radially differently dimensioned cartridges within the pathway and substantially co-axially align the corresponding one of the plurality of radially differently dimensioned cartridges with the cartridge piercing needle, whereby mounting of a respective adapter collar of the plurality of adapter collars within the pathway enables usage of the injector with the corresponding one of the plurality of radially differently dimensioned cartridges,
wherein each adapter collar of the plurality of adapter collars comprises a disk, wherein each adapter collar of the plurality of adapter collars further comprises fingers that are cantilevered, angularly spaced apart from each other, and that project from the disk, the fingers being oriented in an unbiased, radially inwardly projecting closed position covering the cartridge piercing needle, and the fingers being deflectable distally and radially outwardly relative to one another by the corresponding one of the plurality of radially differently dimensioned cartridges into an open position exposing the cartridge piercing needle upon advancement of the corresponding one of the plurality of radially differently dimensioned cartridges through the disk, and wherein in the unbiased, radially inwardly projecting closed position the finders of each adapter collar of the plurality of adapter collars extend radially inwardly to positions that are radially between a central axis of the disk of each corresponding adapter collar and an inner wall of a neck of the corresponding one of the plurality of radially different dimensioned cartridges.

18. The injector device kit of claim 17, wherein each adapter collar of the plurality of adapter collars comprises ribs that are angularly spaced apart from each other and that project radially inwardly from the disk, the ribs being configured to engage the portion of the corresponding one of the plurality of radially differently dimensioned cartridges.

19. The injector device kit of claim 17, wherein the fingers of each adapter collar are connected to one another in the unbiased, radially inwardly projecting closed position by a frangible ring, the frangible ring defining a pre-set breaking force which must be exceeded to separate and disconnect the fingers from one another and deflect the fingers from the unbiased, radially inwardly projecting closed position to the open position.

* * * * *